(12) United States Patent
Mazurowski

(10) Patent No.: US 10,980,519 B2
(45) Date of Patent: Apr. 20, 2021

(54) SYSTEMS AND METHODS FOR EXTRACTING PROGNOSTIC IMAGE FEATURES

(71) Applicant: DUKE UNIVERSITY, Durham, NC (US)

(72) Inventor: Maciej Mazurowski, Durham, NC (US)

(73) Assignee: Duke University, Durham, NC (US)

( * ) Notice: Subject to any disclaimer, the term of this patent is extended or adjusted under 35 U.S.C. 154(b) by 1305 days.

(21) Appl. No.: 15/209,212

(22) Filed: Jul. 13, 2016

(65) Prior Publication Data

US 2017/0014108 A1 Jan. 19, 2017

Related U.S. Application Data

(60) Provisional application No. 62/192,357, filed on Jul. 14, 2015.

(51) Int. Cl.

| | | |
|---|---|---|
| *G01R 33/56* | (2006.01) | |
| *A61B 10/00* | (2006.01) | |
| *G06T 7/00* | (2017.01) | |
| *A61B 5/055* | (2006.01) | |
| *A61B 5/00* | (2006.01) | |

(52) U.S. Cl.
CPC ...... *A61B 10/0041* (2013.01); *G01R 33/5608* (2013.01); *G06T 7/0012* (2013.01); *A61B 5/055* (2013.01); *A61B 5/4312* (2013.01); *A61B 5/4842* (2013.01); *A61B 2576/02* (2013.01); *G01R 33/5607* (2013.01); *G06T 2207/10088* (2013.01); *G06T 2207/30068* (2013.01)

(58) Field of Classification Search
CPC .................................................. G01R 33/5608
See application file for complete search history.

(56) References Cited

U.S. PATENT DOCUMENTS

| | | | |
|---|---|---|---|
| 7,514,209 B2 | 4/2009 | Dai et al. | |
| 7,903,853 B2 * | 3/2011 | Muradyan | ................. G06T 5/50 |
| | | | 382/128 |
| 2004/0101181 A1 * | 5/2004 | Giger | ................... G06T 7/0012 |
| | | | 382/128 |

(Continued)

FOREIGN PATENT DOCUMENTS

| | | | | |
|---|---|---|---|---|
| WO | WO-2006/052731 | | 5/2006 | |
| WO | WO-2007105107 A2 * | 9/2007 | ............. G06T 7/174 |
| WO | WO-2016042037 A1 * | 3/2016 | ............... G06T 5/50 |

OTHER PUBLICATIONS

Giess et al, Background Parenchymal Enhancement at Breast MR Imaging: Normal patterns, diagnostic challenges and potential for false-positive and false-negative interpretation, Jan. 1, 2014, RadioGraphics, Breast Imaging, 234-247 (Year: 2014).*

(Continued)

*Primary Examiner* — Rochelle D Turchen
(74) *Attorney, Agent, or Firm* — Womble Bond Dickinson (US) LLP

(57) ABSTRACT

Described herein are systems and methods for extracting image features from magnetic resonance imaging scans. These methods and systems are useful for both determining cancer lesion severity and disease prognosis. In particular, methods and systems are provided herein for extracting and analyzing imaging features that are correlated with breast cancer subtype and prognosis.

24 Claims, 6 Drawing Sheets

(56) References Cited

U.S. PATENT DOCUMENTS

| | | | | |
|---|---|---|---|---|
| 2005/0234570 | A1* | 10/2005 | Horsch | G06F 19/321 700/93 |
| 2008/0285830 | A1* | 11/2008 | Hong | G06T 7/0012 382/131 |
| 2010/0329529 | A1* | 12/2010 | Feldman | G06K 9/4619 382/131 |
| 2011/0243417 | A1* | 10/2011 | Madabhushi | G06K 9/3233 382/131 |
| 2012/0189176 | A1* | 7/2012 | Giger | G06T 7/0016 382/128 |
| 2013/0202173 | A1* | 8/2013 | Buckler | G06T 7/12 382/131 |
| 2016/0314580 | A1* | 10/2016 | Lloyd | G06T 7/0012 |
| 2016/0364878 | A1* | 12/2016 | Guo | G06T 7/11 |
| 2017/0061087 | A1* | 3/2017 | Boroczky | G06F 16/5866 |
| 2017/0150941 | A1* | 6/2017 | Jago | G06T 7/0012 |

OTHER PUBLICATIONS

DeMartini et al, Background Parenchymal Enhancement on Breast MRI: Impact on Diagnostic Performance, Apr. 2012, Woman's Imaging, AJR:198, W373-W380 (Year: 2012).*

"Comprehensive Molecular Portraits of Human Breast Tumours," *Nature* 490, 61-70 (Oct. 4, 2012).

Bhooshan et al., "Cancerous Breast Lesions on Dynamic Contrast-enhanced MR Images: Computerized Characterization for Image-based Prognostic Markers," Radiology, Mar. 2010; 254(3); pp. 680-690.

Chen et al., "Computerized Interpretation of Breast MRI: Investigation of Enhancement-Variance Dynamics," Medical Physics 31, 1076 (2004); pp. 1076-1082.

Haralick et al., "Textual Features for Image Classification," IEEE Transactions on Systems, Man and Cybergenetics, vol. SMC-3, No. 6, Nov. 1973, pp. 610-621.

Hayashi et al., "Analysis of Complete Response by MRI Following Neoadjuvant Chemotherapy Predicts Pathological Tumor Responses Differently for Molecular Subtypes of Breast Cancer," Oncol Lett., Jan. 2013;5(1); pp. 83-89.

Huber et al., "Breast Cancer Molecular Subtypes in Patients with Locally Advanced Disease: Impact on Prognosis, Patterns of Recurrence, and Response to Therapy," Semin Radiat Oncol., Oct. 2009;19(4); pp. 204-210.

Kim et al., "Histogram Analysis of Apparent Diffusion Coefficient at 3.0T: Correlation With Prognostic Factors and Subtypes of Invasive Ductal Carcinoma," Wiley Periodicals, vol. 42, No. 6, 2015, pp. 1666-1678.

Mazurowski et al., "Radiogenomic Analysis of Breast Cancer: Luminal B Molecular Subtype Is Associated with Enhancement Dynamics at MR Imaging," Radiology: vol. 273: No. 2, Nov. 2014, pp. 365-372.

Paik et al., "A Multigene Assay to Predict Recurrence of Tamoxifen-Treated, Node-Negative Breast Cancer," N Engl J Med; 2004; 351; pp. 2817-2826.

Pal et al., "On Cluster Validity for the Fuzzy c-Means Model," IEEE Transactions on Fuzzy Systems. vol. 3, No. 3, Aug. 1995, pp. 370-379.

Sled et al., "A Nonparametric Method for Automatic Correction of Intensity Nonuniformity in MRI Data," IEEE Transactions on Medical Imaging, vol. 17, No. 1, Feb. 1998, pp. 87-97.

Sledge et al., "Past, Present, and Future Challenges in Breast Cancer Treatment," Journal of Clinical Oncology, vol. 32, No. 19 Jul. 1, 2014: pp. 1979-1986.

Van De Vuver et al., "A Gene-Expression Signature as a Predictor of Survival in Breast Cancer," N Engl J Med; 2002; 347; pp. 1999-2009.

* cited by examiner

SYSTEMS AND METHODS FOR EXTRACTING PROGNOSTIC IMAGE FEATURES

CROSS-REFERENCE TO RELATED APPLICATIONS

This application claims priority to U.S. Provisional Patent Application No. 62/192,357, filed Jul. 14, 2015, the contents of which are hereby fully incorporated by reference.

FIELD OF THE INVENTION

Described herein are systems and methods for extracting image features from magnetic resonance imaging scans. These methods and systems are useful for both determining cancer lesion severity and disease prognosis. In particular, methods and systems are provided herein for extracting and analyzing imaging features that are correlated with breast cancer subtype and prognosis.

BACKGROUND OF THE INVENTION

Breast cancer is a leading cancer diagnosis among women, with over 230,000 new cases a year in the United States. Breast cancer comprises a diverse collection of diseases with varying histologic subtypes, clinical presentations, and treatment responses. Gene expression profiling has been used to attempt to provide some organization to this collection by differentiating breast cancers into molecular subtypes on the basis of similarities between tumors at the genetic level. Advances in this field have resulted in the classification of breast cancer into four distinct molecular subtypes: luminal A, luminal B, human epidermal growth factor receptor 2 (HER2) enriched, and basal-like. These subtypes are unevenly distributed among women with breast cancers with differences according to race, menopausal status, and age. These distinct differences in tumor genetics have different patterns of disease expression, response to therapy, and patient survival outcomes.

The initial presentation of disease and subsequent metastatic spread are influenced by molecular subtype. For example, patients with HER2 enriched tumors have higher rates of nodal involvement, multifocal disease, intraductal components, and lymphovascular invasion than do patients with luminal A tumors. Patients with luminal A and B cancers are more likely to develop bone metastases than are those with the basal-like subtype, who are more likely to develop lung and brain lesions. Molecular subtypes also have shown differences in response to therapeutic interventions. In general, HER2 enriched cancers are more likely to have a complete pathologic response to preoperative chemotherapy. In comparison, luminal A and B cancers show improved response rates to post mastectomy radiation therapy. The luminal B subtype has been shown to have significantly worse relapse-free survival rates than the luminal A subtype, with the increased risk limited to the early period after surgery. Although both luminal A and B subtypes have estrogen receptors (ERs) or progesterone receptors (PRs), the luminal B subtype has been shown to be relatively insensitive to endocrine therapies. These differences in molecular subtype patterns of disease extent and treatment response have subsequent effects on patient survival outcomes and theoretically could be used to help guide initial treatment planning and imaging followup.

Although differentiation of breast cancer into molecular subtypes is a potentially powerful tool to enable clinicians to better guide therapeutic interventions, genetic analysis presents a high barrier because of the cost, specialized equipment, and technical expertise needed to process each sample. As a result, formal molecular subtype analysis is currently neither practical nor cost efficient for all patients with breast cancer. There is a great deal of interest in identifying surrogate markers for individual molecular subtypes. The most widely established method is the use of immunohistochemical surrogates to replace formal genetic analysis. The immunohistochemical markers for ER, PR, and HER2 status have been used to define molecular subtypes: ER- or PR-positive and HER2-negative subtypes for luminal A, ER- or PR-positive and HER2-positive subtypes for luminal B, ER- and PR-negative and HER2-positive subtypes for HER2-enriched, and ER-, PR-, and HER2-negative subtypes for basal-like cancers. The use of surrogates has many advantages, including lower cost, no additional testing, and the ability to pursue hypothesis driven research on a scale larger than would be feasible with genetic analysis; however, the use of surrogates has been shown to be less robustly predictive of outcomes than is formal genetic analysis, and the concordance for molecular subtype classification between immunohistochemical surrogates and formal genetic analysis ranges from 41% to 100%. As a result, there is a demand for additional alternative methods that can allow differentiation of breast cancer into molecular subtypes.

Breast cancer subtype analysis is important for establishing initial treatment regimens, but clinicians must also make complicated decisions regarding how, when, and if to utilize chemotherapy, endocrine therapy, radiation therapy, and/or surgery. This treatment planning is currently dictated by patient age, tumor characteristics, tumor subtype as discussed above, and disease extent, as older patients with more limited disease may benefit from a more conservative course of action and younger patients with more extensive disease may need more aggressive therapies. These variables are associated with patient survival statistics, and there are multiple online breast cancer survival calculators freely available to clinicians to facilitate discussions with patients and guide treatment planning. These calculators rely on information that is patient specific (e.g., age, hormone receptor status) which only allows for generalizable conclusions.

Thus, there is a need for tools, which may be used as a rapid method for noninvasively categorizing breast cancer subtypes and provide prognostic value regarding treatment regimens and patient refractory free and overall survival. Specifically, because preoperative breast magnetic resonance imaging is an important part of the diagnostic workup for many patients there is a need for tools, which incorporate information from MRI imaging studies and improve both diagnostic and prognostic accuracy.

SUMMARY OF THE INVENTION

Described herein are compositions, systems, and methods for extracting image features from cancer lesion preoperative MR images. In some embodiments described herein are methods for the semi-automatic computer aided extraction of MRI features, which may be quantitated. Specifically, the methods and systems described here are useful for determining different breast cancer subtypes and disease prognosis based upon image feature analysis from preoperative MRI. One embodiment described herein is a method of treating a subject having a breast cancer disease comprising one or more breast cancer lesions comprising a) ordering a clinical test comprising evaluating one or more detected breast cancer lesions from an MR image of a breast tissue from the subject, wherein the evaluation comprises: (i) marking one or more boundaries of one or more of the detected breast cancer lesions in the MR image of one or more areas of the breast tissue comprising the one or more breast cancer lesions; (ii) correcting non-uniformity of intensity of the MR image; (iii) segmenting the breast MR image into one or more tissue segments, wherein the tissue segments comprise one or more than one of a normal background parenchyma, the breast cancer lesion, or other breast tissue; (iv) extracting one or a plurality of image features from the MR image; and (v) outputting a score based on the one or plurality of image features, wherein the score indicates one or more clinical outcomes comprising a likelihood of the breast cancer disease progression, an overall survival of the subject, a recurrence-free survival, a distant recurrence-free survival, a response to neo-adjuvant therapy or a combination of clinical outcomes thereof; and b) treating the patient based on the results of the score, wherein treating comprises initiating a standard of care medical treatment, increasing a medical treatment, decreasing a medical treatment, altering a medical treatment, or ceasing a medical treatment.

Another embodiment described herein is a method of predicting a likelihood of breast cancer disease progression or recurrence comprising evaluating one or more detected breast cancer lesions from an MR image of a breast tissue from a subject comprising the steps of: (a) marking one or more boundaries of one or more of the detected breast cancer lesions in the MR image of one or more areas of the breast tissue comprising the one or more breast cancer lesions; (b) correcting non-uniformity of intensity of the MR image; (c) segmenting the breast MR image into one or more tissue segments, wherein the tissue segments comprise one or more than one of a normal background parenchyma, the breast cancer lesion, or other breast tissue; (d) extracting one or a plurality of image features from the MR image; and (e) outputting a score based on the one or plurality of image features; wherein the score indicates the likelihood of the breast cancer disease progression or recurrence.

In some aspects, correcting non-uniformity of intensity comprises performing a nonparametric non-uniform intensity normalization method on the marked MR image.

In some aspects, the one or more tissue segments comprise a normal breast tissue, a normal background parenchyma, and the breast cancer lesion.

In some aspects, the normal parenchyma segmentation is based on fat-saturated MRI images, non-fat saturated MRI images, or both.

In some aspects, the normal breast tissue segment is obtained by performing a global thresholding method on the MR image.

In some aspects, the normal background parenchyma and the breast cancer lesion segments are obtained by performing Fuzzy C-Means clustering.

In some aspects, the score comprises a multivariate biomarker defined by a combination of extracted features, and wherein the extracted features are one or more features selected from the group consisting of (a) enhancement-based features for breast cancer lesion, normal breast parenchyma, or both; (b) texture features; (c) size features; (d) shape features, both 2 dimensional and 3 dimensional; (e) gradient features; (f) dynamic features; (g) features quantifying imaging-based heterogeneity of the breast cancer lesions; and (h) features quantifying spatial kinetics of the breast cancer lesions.

In some aspects, the one or more size and shape features comprise one or more of a major axis length, a minor axis length, a mean radius length, a standard deviation of the radius length, a volume of the breast cancer lesion, and a volume of the normal background parenchyma, circularity, and features based on three-dimensional analysis of the images.

In some aspects, the one or more gradient features comprise a mean and a standard deviation of one or more intensity gradients of one or more breast cancer lesion boundary voxels. In some aspects, the one or more texture features comprises at least one or more Haralick texture features.

In some aspects, the one or more dynamic features comprise a feature F1 with different parameters, a feature F2 with different parameters, peak location or any combination thereof.

In some aspects, feature F1 comprises a ratio of an average breast cancer lesion image enhancement to a maximal breast cancer lesion image enhancement at a time point when a volume of a background parenchyma image enhancement reaches a predetermined threshold. In some aspects, feature F2 comprises a portion of a background parenchyma image enhancement at a time point when the average breast cancer lesion enhancement divided by the maximum of average breast lesion enhancement reaches a predetermined threshold. In some aspects, feature F1 and feature F2 is calculated according to Formula I or Formula II, respectively:

$$F1 = \frac{E^{tumor}(V_{T_{12}}^{parenchyma}(t) = T_{11})}{E_{max}^{tumor}} \quad \text{Formula I}$$

$$F2 = V_{T_{22}}^{parenchyma}\left(\frac{E^{tumor}(t)}{E_{max}^{tumor}} = T_{21}\right) \quad \text{Formula II}$$

wherein for Formulae I and II:

$$E^{tumor}(t) = \frac{I^{tumor}(t) - I_{pre}^{tumor}}{I_{pre}^{tumor}}$$

$$V_{T_{22}}^{parenchyma}(t) = \frac{n(E^{parenchyma}(t) > T_{22} \cdot E_{max}^{tumor})}{n^{parenchyma}}$$

$$E^{parenchyma}(t) = \frac{I^{parenchyma}(t) - I_{pre}^{parenchyma}}{I_{pre}^{parenchyma}}$$

and wherein $T_{11}$, $T_{12}$, $T_{21}$, and $T_{22}$ may each range from 0-1.

In some aspects, $T_{11}$ is 0.05 and $T_{12}$ is 0.5 or $T_{11}$ is 0.05 and $T_{12}$ is 0.1. In some aspects, $T_{21}$ is 0.8 and $T_{22}$ is 0.5 or $T_{21}$ is 0.5 and $T_{22}$ is 0.1. In some aspects, a higher value of feature F1 is indicative of an increased risk of breast cancer disease progression.

In some aspects, a value of the feature F1 greater than 0.75 is indicative of an increased risk of breast cancer disease recurrence.

In some aspects, the one or more clinical outcomes is determined for a subject with a breast cancer that is a luminal A, luminal B, HER2-positive, basal, normal-like, or claudin-low breast cancer molecular subtype.

In some aspects, a value of feature F1 greater than 0.75 combined with the situation wherein the time point at which enhancement of the breast cancer lesion reaches its peak value occurs before the time point of the second post-contrast sequence, together are indicative of luminal A or luminal B breast cancer.

In some aspects, the dynamic feature is a feature F, wherein F is calculated according to Formula III:

$$F = \frac{E^{TUM,avg}\left(\min\{t: V_{T_1}^{BP}(t) = T_2\}\right)}{\max_t(E^{TUM,avg}(t))};$$

wherein $$V_{T_1}^{BP}(t) = \frac{\left|(x,y,z) \in BP : E(x,y,z,t) > T_1 \cdot \max_t(E^{TUM,avg}(t))\right|}{|BP|}$$

$$E^{TUM,avg}(t) = \frac{\Sigma_{x,y,z \in TUM} E(x,y,z,t)}{|TUM|}$$

$$E(x,y,z,t) = \frac{I(x,y,z,t) - I(x,y,z,0)}{I(x,y,z,0)};$$

and, wherein $T_1=0.1$ and $T_2=0.05$; or $T_1=0.5$ and $T_2=0.02$; or $T_1=0.5$ and $T_2=0.05$; or $T_1=0.5$ and $T_2=0.1$ or $T_1=0.8$ and $T_2=0.05$ or $T_1=0.8$ and $T_2=0.1$.

In some aspects, the medical treatment comprises chemotherapy, hormonal therapy, immunotherapy or combinations thereof.

In some aspects, the score, alone or in combination with genomic and pathological profile, is used to determine if patients will receive chemotherapy.

In some aspects, the score is combined with one or more than one of cancer lesion receptor status, cancer lesion receptor status-based lesion subtype, lesion size, lymph node involvement, OncotypeDX® marker, Mammaprint® marker, PAM50 marker, lesion pathology, and other tumor markers and/or genomic markers.

In some aspects, one or more clinical outcomes is determined for a subject having a breast cancer that is a lymph-node positive breast cancer or a subject having a breast cancer that is a lymph-node negative breast cancer.

In some aspects, one or more clinical outcomes is determined for a subject that has a breast cancer that is luminal A, luminal B, basal, normal-like or claudin-low.

In some aspects, one or more clinical outcomes is determined for a subject that has a breast cancer that has a known molecular subtype comprising an ER-positive or -negative, PR-positive or -negative, HER2-positive or -negative, or a triple negative breast cancer or a breast cancer having any other combination of ER, PR, or HER2 receptors.

In some aspects, a value of feature F greater than or equal to 0.75 is prognostic of recurrence-free survival.

In some aspects, the one or more clinical outcomes is determined for a subject in menopause or not in menopause.

In some aspects, the one or more clinical outcomes is determined for a subject with an age that is within an age range group, wherein the age range group lies in between 10 years of age and 99 years of age.

Another embodiment described herein is a method of identifying one or more breast cancer subtypes of one or more detected breast cancer lesions from an MR image of a breast tissue from a subject comprising the steps of: (a) marking one or more boundaries of one or more of the detected breast cancer lesions in the MR image of one or more areas of the breast tissue comprising the one or more breast cancer lesions; (b) correcting non-uniformity of intensity of the MR image; (c) segmenting the breast MR image into one or more tissue segments; (d) extracting one or a plurality of image features from the MR image; (e) outputting a score based on the one or plurality of image; wherein the score is indicative of one or more subtypes of breast cancer.

In some aspects, one or more imaging features selected from Table 5 is indicative of one or more breast cancer subtypes comprising a luminal A breast cancer, a luminal B breast cancer, a HER2-positive breast cancer, or a basal breast cancer. In some aspects, a higher value of feature F1 and a peak location value are indicative of luminal A or luminal B breast cancer.

Another embodiment described herein is a system useful in identifying a breast cancer subtype and predicting a likelihood of breast cancer disease progression or recurrence prognosis in a subject from one or more MR images of a detected breast cancer lesion from the subject, the system comprising: at least a computer comprising: (a) one or more MR images of the detected breast cancer lesion; (b) an interface connected with the computer for marking one or more boundaries of one or more detected breast cancer lesions in the MR image of one or more areas of a tissue comprising the one or more breast cancer lesions; (c) a programming configured to automatically: (i) correct non-uniformity of intensity of the MR image; (ii) segment the MR image into one or more tissue segments; (iii) extract one or a plurality of the image features from the MR image, wherein at least one of the plurality of image features is a dynamic image feature that compares the average breast cancer lesion image enhancement to a maximal breast cancer lesion image enhancement at a time point when a volume of a background parenchyma image enhancement reaches a predetermined threshold; and (iv) provide a score of the one or plurality of the extracted image features, wherein the score is useful in the identifying the breast cancer subtype and/or the predicting the likelihood of breast cancer disease progression or recurrence.

Another embodiment described herein is a non-transitory computer-readable medium with instructions stored thereon that, when executed by a computer processor, performs the steps comprising: (a) correcting non-uniformity of intensity of a MR image; (b) segmenting the MR image into one or more tissue segments; (c) extracting one or a plurality of the image features from the MR image, wherein at least one of the plurality of image features is a dynamic image feature that compares an average cancer lesion image enhancement to a maximal cancer lesion image enhancement at a time point when a volume of a background parenchyma image enhancement reaches a predetermined threshold; and (d) converting the one or plurality of extracted image features into a single diagnostic score that is useful in predicting a likelihood of a cancer disease progression or recurrence.

Another embodiment described herein is a computer-implemented method for identifying a breast cancer subtype and predicting a likelihood of breast cancer disease progression or recurrence prognosis in a subject from one or more MR images of a detected breast cancer lesion from the subject, the method comprising the steps of (a) marking one or more boundaries of one or more detected breast cancer lesions in the MR image of one or more areas of a tissue comprising the one or more breast cancer lesions; (b) correcting non-uniformity of intensity of the MR image; (c) segmenting the MR image into one or more tissue segments; (d) extracting one or a plurality of the image features from the MR image, wherein at least one of the plurality of image features is a dynamic image feature that compares the average breast cancer lesion image enhancement to a maximal breast cancer lesion image enhancement at a time point when a volume of a background parenchyma image enhancement reaches a predetermined threshold; and (e) converting the one or plurality of extracted image features into a single diagnostic score that is useful in the identifying the breast cancer subtype and the predicting the likelihood of breast cancer disease progression or recurrence.

DETAILED DESCRIPTION OF THE INVENTION

Figure 1:
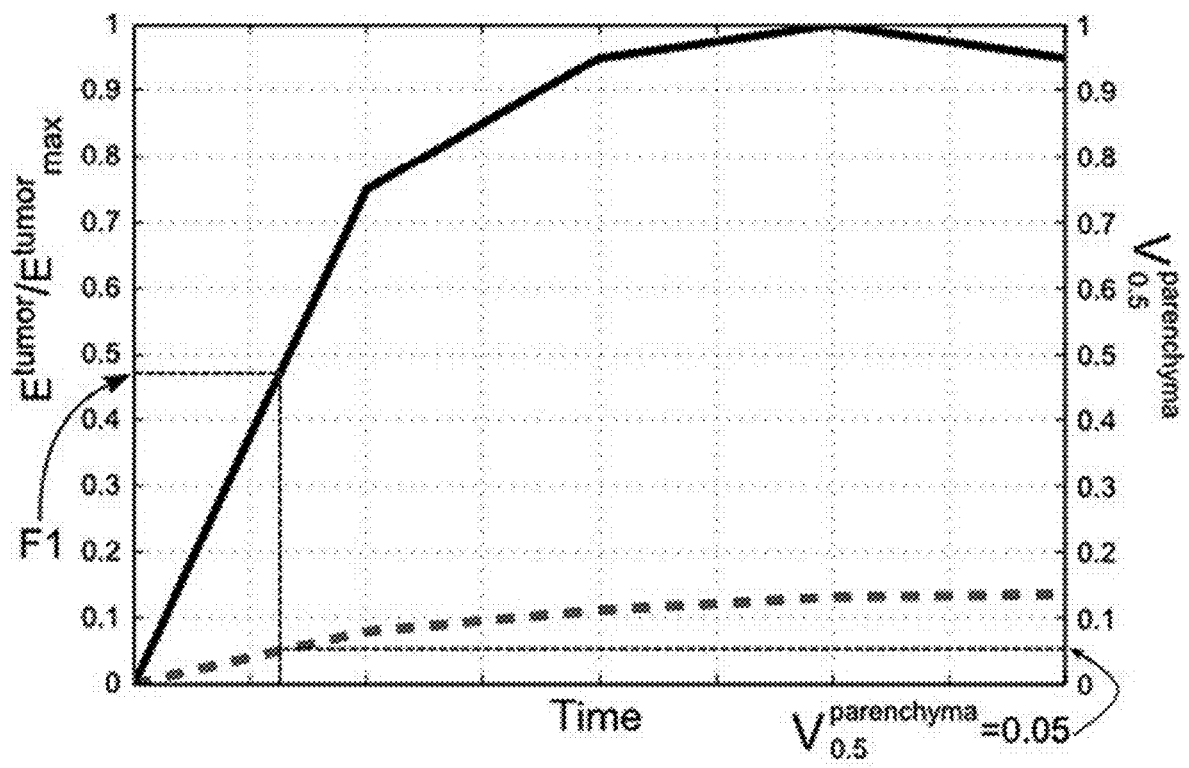
FIG. 1. Graph illustrating the extraction of dynamic feature F1 with parameters T11=0.05 and T12=0.5. First, the time when volume of enhancing background parenchyma reaches 0.05 of total background parenchyma volume is determined (dashed line). Then, enhancement of tumor at that time is found (solid line); equal to F1.

Described herein are systems and methods for extracting breast imaging features, which distinguish one or more of the molecular subtypes of breast cancer based on extracted image features and provide prognostic information.

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used herein, an "individual" or "subject" can be a "patient." A "patient" refers to an "individual" who is under the care of a treating physician. The patient can be male or female.

A "patient sub-population," and grammatical variations thereof, as used herein, refers to a patient subset characterized as having one or more distinctive measurable and/or identifiable characteristics that distinguishes the patient subset from others in the broader disease category to which it belongs.

As used herein, "predicting" and "prediction" does not mean that the outcome is occurring with 100% certainty. Instead, it is intended to mean that the outcome is more likely occurring than not. Acts taken to "predict" or "make a prediction" can include the determination of the likelihood that an outcome is more likely occurring than not. Assessment of multiple factors described herein can be used to make such a determination or prediction.

As used herein, "treatment" refers to clinical intervention in an attempt to alter the natural course of the individual being treated. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving improved prognosis.

The term "substantially" as used herein means to a great or significant extent, but not completely.

As used herein, "a" or "an" means one or more unless otherwise specified.

Terms such as "include," "including," "contain," "containing," "has," or "having," and the like, mean "comprising."

The methods and systems described herein allow for the semi-automatic extraction of image features and analysis. The automatic segmentation and feature analysis as described herein allows for a detailed analysis of images without increasing the time burden for an interpreting radiologist or clinician. The automatic segmentation and extraction of imaging features using the methods and systems described herein provide for a high level of reproducibility that is not limited by inter- or intra-observer variability. Additionally, the methods and systems described herein provide reliable image feature extraction results that may be useful for determining breast cancer molecular subtype and indicate prognosis that are independent of imaging center or institution, patient age, tumor grade or size, imaging protocol, and clinician.

The prognostic information provided by the image features described herein may more accurately predict the likelihood of disease progression or recurrence. This information may aid in treatment planning and assist in patient discussions regarding treatment expectations and guide future research efforts.

In some embodiments described herein, a plurality of image features are extracted by using the systems and methods described herein. In some embodiments described herein, the plurality of extracted image features may be used to distinguish breast cancer subtype and predict disease aggressiveness or progression. The plurality of image features may comprise one or more tumor image features relating to size, shape, gradient, texture, and dynamic tumor/parenchyma image enhancement features as described herein. The dynamic features relate to rate of the enhancement dynamics of the tumor to the background parenchymal enhancement. See, Grimm et al., *J. Magn. Reson. Imaging* (2015) and Mazurowski et al., *Radiology* 273(2) 365-372 (2014), each of which is incorporated by reference herein in their entirety.

Some embodiments described herein provide for systems and methods for differentiating between luminal A and luminal B breast cancers. Differentiating between these two luminal breast cancer subtypes is an important step in effective treatment planning. The luminal A subtype is less aggressive with greater sensitivity to endocrine and radiation therapies as well as better prognosis. In contrast, luminal B subtype is more aggressive with worse response rates to endocrine and chemotherapy and demonstrates poor relapse free survival rates.

In some embodiments, the systems and methods described herein may distinguish the luminal B molecular subtype from other molecular breast cancer subtypes (e.g., Luminal A, HER2, and basal). Accordingly, using the methods of image feature extraction and analysis as described herein, it was found that there is a large differential between the rate of enhancement of luminal B breast cancer and the normal background parenchyma. In some aspects, the imaging features are obtained from routine breast MR imaging scans. Without being bound by any theory, it is thought that this difference may suggest increased vascularity or vascular permeability that is associated with luminal B breast tumors. In some aspects, the image feature F1 (parameters 1) as measured and calculated using the image feature extraction methods as described herein may distinguish luminal B breast cancer tumors from other molecular breast cancer subtypes.

In some embodiments, the systems and methods described herein may distinguish both luminal A and luminal B molecular subtype from other molecular breast cancer subtypes (e.g., HER2 and basal). In some aspects, luminal A and luminal B molecular subtypes are associated with computerized MRI features relating enhancement dynamics described herein of the tumor with the background parenchymal enhancement. In some aspects, imaging feature F1 (parameters 2) as measured using the image feature extraction methods as described herein can distinguish both luminal A and luminal B molecular subtypes from other molecular breast cancer subtypes. In some aspects, the peak location image as measured using the image feature extraction methods as described herein can distinguish both luminal A and luminal B molecular subtypes from other molecular breast cancer subtypes.

In some embodiments described herein, one or more image features selected from Table 5 measured using the methods described herein may be used to distinguish luminal A breast cancer.

In some embodiments described herein, one or more image features selected from Table 2 or Table 5 may be used to distinguish luminal B breast cancer.

In some embodiments described herein, one or more image features selected from Table 5 measured using the methods described herein may be associated with HER2-positive breast cancer.

In some embodiments described herein, one or more image features selected from Table 5 measured using the methods described herein may be associated with basal breast cancer.

In some embodiments described herein, the systems and methods described herein provides a predictive value for breast cancer progression free survival. In some aspects, progression free survival may be predicted by measuring the image feature F1 as described herein. In some aspects, higher feature values are associated with increased risk of disease progression. Thus, in some aspects, an increase in the relative tumor enhancement rate corresponds to an increase in the risk of cancer recurrence.

In some embodiments described herein, the dynamic enhancement feature F1 may be determined using Formula I and the dynamic enhancement feature F2 may be determined using Formula II.

$$F1 = \frac{E^{tumor}\left(V_{T_{12}}^{parenchyma}(t) = T_{11}\right)}{E_{max}^{tumor}} \quad \text{Formula I}$$

$$F2 = V_{T_{22}}^{parenchyma}\left(\frac{E^{tumor}(t)}{E_{max}^{tumor}} = T_{21}\right) \quad \text{Formula II}$$

wherein for Formulae I and II above:

$$E^{tumor}(t) = \frac{I^{tumor}(t) - I_{pre}^{tumor}}{I_{pre}^{tumor}}$$

$$V_{T_{22}}^{parenchyma}(t) = \frac{n(E^{parenchyma}(t) > T_{22} \cdot E_{max}^{tumor})}{n^{parenchyma}}$$

$$E^{parenchyma}(t) = \frac{I^{parenchyma}(t) - I_{pre}^{parenchyma}}{I_{pre}^{parenchyma}}$$

In Formulas I and II above, $I_{pre}^{tumor}$ and $I_{pre}^{parenchyma}$ are the average intensity values of the tumor and background parenchyma on pre-contrast T1-weighted images. $I^{tumor}(t)$ and $I^{parenchyma}(t)$ are the average intensities of the tumor and background parenchyma at the time t. $E^{tumor}(t)$ and $E^{parenchyma}(t)$ are the enhancement of the tumor and parenchyma at the time t. $E_{max}^{tumor}$ is the maximum enhancement of the tumor at all the time points. $n^{parenchyma}(t)$ is the total number of background breast parenchyma voxels. $n(E^{parenchyma}(t) > T_{22} \cdot E_{max}^{tumor})$ is the number of voxels such that enhancement of the background parenchyma for the voxel is larger than $T_{22} \cdot E_{max}^{tumor}$ ($T_{22}$ is a constant threshold) at time point t, $V_{T_{22}}^{parenchyma}(t)$ is the fraction of all voxels in the background parenchyma such that enhancement of the background parenchyma for the voxel is larger than $T_{22} \cdot E_{max}^{tumor}$ at time point t. Furthermore, $$V_{T_{22}}^{parenchyma}\left(\frac{E^{tumor}(t)}{E_{max}^{tumor}} = T_{21}\right)$$

is $V_{T_{22}}^{parenchyma}$ at the time t when $V_{T_{12}}^{parenchyma}$ reaches a predefined threshold of $T_{11}$.

In some embodiments described herein, the values for parameters $T_{11}$, $T_{12}$, $T_{21}$, and $T_{22}$ are selected on the basis of the expected levels of enhancement of the tumor lesion and background parenchyma. In some aspects, the parameters for $T_{11}$, $T_{12}$, $T_{21}$, and $T_{22}$ may each range from 0-1, including each integer within the specified range. In some aspects, values comprise F1 parameters 1: $T_{11}$=0.05, $T_{12}$=0.5. In some aspects, values comprise F2 parameters 1: $T_{21}$=0.8, $T_{22}$=0.5. In some aspects, the values comprise F1 parameters 2: $T_{11}$=0.05, $T_{12}$=0.1. In some aspects, values comprise F2 parameters 2: $T_{21}$=0.5, $T_{22}$=0.1.

In some embodiments described herein, the dynamic enhancement feature F may be determined using Formula III.

$$F = \frac{E^{TUM,avg}\left(\min\{t: V_{T_1}^{BP}(t) = T_2\}\right)}{\max_{t}(E^{TUM,avg}(t))}$$

wherein $$V_{T_1}^{BP}(t) = \frac{\left|(x, y, z) \in BP: E(x, y, z, t) > T_1 \cdot \max_{t}(E^{TUM,avg}(t))\right|}{|BP|}$$

$$E^{TUM,avg}(t) = \frac{\sum_{x,y,z \in TUM} E(x, y, z, t)}{|TUM|}$$

-continued $$E(x, y, z, t) = \frac{I(x, y, z, t) - I(x, y, z, 0)}{I(x, y, z, 0)}$$

and, wherein $T_1=0.1$ and $T_2=0.05$; or $T_1=0.5$ and $T_2=0.02$; or $T_1=0.5$ and $T_2=0.05$; or $T_1=0.5$ and $T_2=0.1$ or $T_1=0.8$ and $T_2=0.05$ or $T_1=0.8$ and $T_2=0.1$.

In the above formulae, $I(x,y,z,t)$ is an intensity of a voxel located at the $(x,y,z)$ coordinates at the time t. TUM is the set of tumor voxels and BP is the set of background parenchyma voxels. $T_1$ and $T_2$ are constant parameters.

In some embodiments described herein are methods and systems for extracting one or more image features from a MR image semi-automatically. In some embodiments, the methods for image feature extraction comprise the steps: (a) establishing the boundary of the lesion; (b) correcting non-uniform image intensity values; (c) segmenting the lesion within the established boundary into segments comprising normal tissue, the normal background parenchyma, and the tumor lesion; (d) extracting one or more or a plurality of different image features described herein; analyzing the plurality of different image features to output a score indicating one or more breast cancer subtypes or clinical prognosis (e.g., progression or disease recurrence). In some aspects, the step (a) is performed manually by a clinician or radiologist. In some aspects, steps (b)-(e) are performed automatically with a computer system comprising a programming of performing the method steps (b)-(e). In some aspects, one or more clinical outcomes or prognosis of a subject may be determined based on the results of the image feature analysis.

In some embodiments described herein, the methods and systems described herein are useful for predicting one or more clinical outcomes comprising breast cancer disease recurrence risk (i.e., recurrence-free survival), disease progression, overall survival of a subject, or a response to neo-adjuvant therapy or a combination of clinical outcomes thereof. In some aspects, the one or more clinical outcomes may be predicted for a subject or group of subjects that is undergoing a current treatment regimen (e.g., a standard of care treatment regimen or next generation treatment regimen). In some aspects, the one or more clinical outcomes may be predicted for a subject or group of subjects that has an identified breast cancer molecular subtype comprising a luminal A, luminal B, HER2-positive, basal, normal-like, or claudin-low breast cancer molecular subtype. In some aspects, the one or more clinical outcomes may be predicted for a subject or group of subjects that has an identified breast cancer receptor status comprising an estrogen receptor-positive or negative (ER-positive or negative), progesterone receptor-positive or negative (PR-positive or negative), HER2-positive or negative, or any combination of ER, PR, or HER2 receptor-positive or -negative breast cancers thereof (e.g., a triple negative breast cancer (TNBC)). In some aspects, the one or more clinical outcomes may be predicted for a subject or group of subjects that have an age or set of ages that fall within a given age range group, wherein the given age range group(s) of the subject or group of subjects is in between 10 years of age to 99 years of age (e.g., age range groups comprising 10-29; 30-45; 46-60; 61-75, or 76-99 years of age). In some aspects, the one or more clinical outcomes may be predicted for a subject in menopause or not in menopause. In some aspects, the one or more clinical outcomes may be predicted for a subject having a breast cancer that is a lymph-node positive breast cancer or a subject having a breast cancer that is a lymph-node negative breast cancer.

In some embodiments described herein, the one or more extracted image features may be further combined with genomic characteristics of the one or more lesions to predict one or more clinical outcomes comprising breast cancer disease recurrence risk (i.e., recurrence-free survival), disease progression, overall survival of a subject, or a response to neo-adjuvant therapy or a combination of clinical outcomes thereof. Exemplary and non-limiting genomic characteristics may comprise gene expression arrays, RNA-sequencing data, whole genome sequencing data, epigenomic data, and the like. For example, known breast cancer gene expression signatures may be used, see, for example, U.S. Pat. No. 7,514,209; Van De Vijver et al., N. Engl. J. Med. 347, 2999-2009 (2002); PCT International Patent Application No. WO2006/052731; and Paik et al., N. Engl. J. Med. 347, 2817-2826 (2004), each of which is incorporated by reference herein for their teachings of gene expression signatures involvement in breast cancer prognosis. In some aspects, data obtained from a commercially available genomic test, such as the Oncotype DX®, or the MammaPrint® test may be combined with the diagnostic score obtained from the analysis of the one or more extracted image features described herein. Oncotype DX® is a registered trademark for a genomic test that analyzes the activity of a group of genes that can affect how a cancer is likely to behave, and is provided by Genomic Health, Inc., 101 Galveston Drive, Redwood City, Calif. 94063. MammaPrint® is a registered trademark for a 70-gene breast cancer recurrence genomic assay provided by Agendia, Inc., 22 Morgan, Irvine, Calif. 92618. In some aspects, pairing genomic data with the MR image feature extraction data as described herein may provide further prognostic information for a subject having one or more breast cancer lesions.

In some embodiments described herein, the one or more extracted image features determined using the methods and systems described herein may be further combined with tumor molecular subtype information comprising luminal A, luminal B, HER2 status, basal, normal-like, or claudin-low breast cancer molecular subtype information to predict one or more clinical outcomes as described herein. In some aspects, the tumor molecular subtype may be determined based on an assessment of the individual receptor status or a combination of receptors of the breast cancer (e.g., ER-positive or -negative, PR-positive or -negative, HER2-positive or -negative, or triple negative). In some aspects, a luminal A cancer may be ER-positive and HER2-negative. In some aspects, a luminal A cancer may be PR-positive and HER2-negative.

In some aspects, a luminal A cancer may be ER-positive and PR-positive and HER2-negative. In some aspects, a luminal B cancer may be ER-positive and HER2-positive. In some aspects, a luminal B cancer may be PR-positive and HER2-positive. In some aspects, a luminal B cancer may be ER-positive, PR-positive, and HER2-positive. In some aspects, a HER2 cancer may be ER-negative, PR-negative and HER2-positive. In some aspects, a basal breast cancer may be may be ER-negative, PR-negative and HER2-negative. In some further aspects, the tumor molecular subtype may be determined based on genome expression data.

In some embodiments, one or more clinical outcomes can be predicted in a multivariate way by a combination of one or more extracted image features as described herein with additional clinical information for a subject or subject group comprising a medical treatment status, tumor molecular subtype, receptor status, age range, menopausal status, or lymph-node status as described herein or a combination of clinical information thereof. In some aspects, a combination of one or more extracted image features, additional clinical information, and genomic expression data as described herein may be used for the multivariate prediction of one or more clinical outcomes. In some aspects, this multivariate combination may be used to generate a diagnostic score indicative of one or more clinical outcomes as described herein.

The embodied methods and systems for extracting one or more image features described herein may be used by a clinician to make a decision regarding a clinical treatment for a subject in need thereof. As described herein, the one or more image features may be further combined with genome expression data or other clinical information as described herein to provide additional prognostic value. In some aspects, one or more of the extracted imaging features as described herein may be used by an interpreting clinician to make a decision regarding a clinical treatment for a subject in need thereof. Thus, a subject in need of treatment thereof may be assigned an optimal treatment regimen based on the results of the image feature analysis comprising initiating a standard of care medical treatment, increasing a medical treatment, decreasing a medical treatment, altering a medical treatment, or ceasing a medical treatment; see, for example, Sledge et al., *J. Clin. Oncol.* 32(19) 1979-1986 (2014), which is incorporated by reference herein for its teachings of breast cancer treatment regimens. For example, any one or more of the image features from Table 2 or Table 5 or their multivariate derivative may be used by an interpreting clinician to make a decision regarding a clinical treatment for a subject in need of treatment thereof.

EXAMPLES

Example 1

Luminal B Breast Tumor Molecular Subtype is Associated with MRI Tumor Enhancement Dynamics I. Study Methods
Patient Population This was an institutional review board approval exempt study of information from a publically available database. We used the Breast Cancer Risk Assessment dataset recently made available by the Cancer Imaging Archive. The Cancer Imaging Archive dataset contains imaging studies for a subset of patients from the Cancer Genome Atlas. The Cancer Genome Atlas database contains full genomic sequencing and clinical data for the patients. The two databases were correlated by using unique patient identifiers.

A fellowship-trained breast imager (S.C.Y., with 9 years of experience reading breast MR images) marked the MR images by drawing a box containing the abnormality. The reader used a graphical user interface developed in our laboratory. The lesions were classified into four genomic subtypes as luminal A, luminal B, HER2-enriched, or basal-like. The subtypes for the patients were obtained from the supplementary materials to an article by the Cancer Genome Atlas Network, see *Nature* 490 (7418) 61-70 (2012), which is incorporated by reference herein in its entirety.

Of the patient data available in the Cancer Imaging Archive, we used data from 48 patients who (a) had subtypes determined according to the Cancer Genome Atlas Network and (b) in whom the reader indicated exactly one lesion in the MR imaging examination results. The second criterion was used to ensure that the imaging and genomic features were for the same lesion. To allow for repeating our experiments, we uploaded the Cancer Genome Atlas identifiers for the patients included in our experiments to the Web site of M.A.M. laboratory at Duke University: (http://deckard.duhs.duke.edu/~mazurowski/data/2014_radiogenomic/tcga_brca_subset_mazurowski_2014.csv).

Imaging Data

All imaging data were obtained from the Breast Cancer Risk Assessment collection of the Cancer Imaging Archive (http://www.cancerimagingarchive.net). Patients were imaged at four different institutions: the Mayo Clinic, the Memorial Sloan Kettering Cancer Center, the Roswell Park Cancer Institute, and the University of Pittsburgh Medical Center. All imaging was performed with 1.5 T MR imagers (Signa, Signa HDx, or Signa Excite; GE; Fairfield, Conn.). Patients underwent T1-weighted precontrast and three to six postcontrast sequences with a gadolinium based contrast agent. Because the imaging studies are publically available, additional information about them can be obtained at the Cancer Imaging Archive (http://www.cancerimagingarchive.net/).

Imaging Features

For each of the lesions, we extracted 23 imaging features on precontrast and postcontrast T1-weighted images by using the bounding box provided by the radiologist (S.C.Y.). Computer vision algorithms were applied to extract all the features automatically. The feature extraction process was composed of three steps: (a) The N3 method (36) was applied on all MR images to correct intensity nonuniformity, see, Sled et al., *IEEE Trans. Med. Imaging* 17(1) 87-97 (1998), which is incorporated by reference herein for its teachings thereof.

(b) The images were segmented into breast, normal background parenchyma, and lesion. The breast region was first segmented by using a thresholding based method after manual removal of the chest wall from the image. Fuzzy C means clustering was adopted to separate the lesion in the region of interest (the bounding box) from the background parenchyma in the breast region automatically, see, for example, Bhooshan et al., *Radiology* 254(3) 680-690 (2010); Chen et al., *Med Phys* 31(5) 1076-1082 (2004); and Pal and Bezdek., *IEEE Trans. Fuzzy Syst* 3(3) 370-379 (1995), each of which is incorporated by reference herein for their teachings of Fuzzy C means clustering. Although the lesion and the background parenchyma were always exclusive, it is possible that the background parenchyma region included nontumor regions in the bounding box. The entire volume of the background parenchyma from the breast containing the abnormality was used for feature calculation.

(c) A total of 23 features were extracted to characterize the detected lesion regions, including 19 lesion features (four geometric features, 14 Haralick texture features, and one kinetic feature) and two new proposed dynamic features (two variations of each). The 14 Haralick texture features were calculated from the gray level co-occurrence matrix of the lesion region to describe its textural properties including contrast (a measurement of the intensity of the contrast between a pixel and an adjacent pixel), correlation (measurement of how adjacent pixels correlate), energy (also known as angular second moment; a measurement of uniformity), and entropy (a measurement of the disorder or complexity of the lesion region), see., Haralick et al., *IEEE Trans. Syst. Man Cybern.* 3(6) 610-621 (1973), which is incorporated by reference herein for its teachings and formulas for calculating "Haralick features."

For both of the proposed dynamic features, we explored two different sets of parameters to evaluate the relationship between enhancement of the lesion and enhancement of the background parenchyma. This resulted in four actual features. These features were calculated automatically by using computer segmented data of the lesion and background parenchyma on the basis of pre- and post-contrast T1-weighted images. We described feature F1 as the average enhancement of the lesion at the time when the volume of the enhancing background parenchyma reaches a certain predefined threshold. An example plot that demonstrates how feature F1 is calculated is shown in FIG. 1. We defined feature F2 as the portion of the background parenchyma that enhances at the time when lesion enhancement reaches a certain predefined level.

Statistical Analysis

We focused on the association of imaging features with specific molecular subtypes. We built a logistic regression analysis separately for each subtype. In the model subtype was a binary variable with the value of 1 when a tumor belonged to the subtype of interest (eg, luminal A) and 0 if it belonged to any other subtype. Our analysis consisted of two steps. First, to evaluate the association of imaging features with specific genomic subtypes, we developed and evaluated multivariate models that used imaging features as independent variables and subtype as a binary dependent variable. The analysis was repeated for the four subtypes: luminal A, luminal B, HER2-enriched, and basal-like tumors. The multivariate logistic regression models were constructed by using the generalized linear model function in the R statistical computing environment (http://www.r-project.org/). Then, the association of the imaging variables with each specific subtype was assessed by using the likelihood ratio test function in R. Because of the small sample size, we reduced the number of features used in this multivariate analysis by removing features that strongly correlated with other features (correlation of 0.5 or more); in each step of this reduction, a pair of features with the highest correlation was selected. If the correlation between the pair of features was 0.5 or more, we also evaluated the average correlation of each of the two features with the other features. The feature with the higher correlation was removed. For this portion of the analysis, we considered a P value of less than 0.05 as indicative of a significant difference.

Second, we performed a detailed analysis of the association of each of the imaging features with specific subtypes. This analysis was limited to the subtypes identified as potentially associated with imaging features in the first step described above. In our detailed analysis, we controlled for three potentially confounding variables: the age of the patients, their menopausal status, and the orientation of the MR images (sagittal vs axial). For each imaging variable, we performed a likelihood ratio test (in R) of the model containing the imaging variable and the confounding variables versus the model with the confounding variables only. This allowed for assessment of the association of the imaging variables with the genomic subtype independently of the confounding variables. Finally, the Bonferroni correction was applied to account for multiple hypothesis testing (tests for 23 imaging features). A P value less than 0.0022 (0.05 of 23) was considered to indicate a significant difference.

II. Study Results

The patient demographic and cancer characteristics are shown in Table 1. In the first step of our analysis, we established the potential for correlation between individual genomic subtypes and imaging features. We excluded the normal-like subtype from this analysis because only one subject belonged in this group. We found an association between the imaging features and the luminal B subtype (P=0.028) but not between the imaging features and other subtypes (P>0.25). Therefore, we focused our detailed analysis on the relationship between imaging features and the luminal B subtype.

The results of our analysis to determine which individual imaging features are associated with the luminal B subtype are shown in Table 2. P values are provided for the likelihood ratio test for a model containing a given imaging variable and the confounding variables (image orientation, menopausal status, and age) versus the model that contains the confounding variables only. After adjustment for multiple hypothesis testing, only one imaging variable remained significant: F1 with the first set of parameters (P=0.0015). Investigation of the relationship between this variable and the likelihood of the luminal B subtype showed that a higher value of F1 indicated a higher likelihood of the luminal B subtype. The relationship between F2 and likelihood of the luminal B subtype was the opposite.

TABLE 1

Patient Demographics and Cancer Characteristics

| Characteristic | All patients (n = 48) | Luminal A (n = 27) | Luminal B (n = 8) | HER2 (n = 4) | Basal-like (n = 8) | Normal-like (n = 1) |
|---|---|---|---|---|---|---|
| Age (y)* | 57.0 (29-82) | 58.7 (39-82) | 58.4 (45-66) | 62.0 (53-79) | 46.5 (29-73) | 64 |
| Race and ethnicity | | | | | | |
| White, not Hispanic | 33 | 15 | 7 | 3 | 7 | 1 |
| White, Hispanic | 1 | 1 | 0 | 0 | 0 | 0 |
| White, ethnicity not reported | 12 | 10 | 0 | 1 | 1 | 0 |
| Black | 2 | 1 | 1 | 0 | 0 | 0 |
| Menopausal status | | | | | | |
| Premenopausal | 15 | 9 | 1 | 0 | 5 | 0 |
| Perimenopausal | 2 | 1 | 1 | 0 | 0 | 0 |
| Postmenopausal | 29 | 15 | 6 | 4 | 3 | 1 |

TABLE 1-continued

Patient Demographics and Cancer Characteristics

| Character-istic | All patients (n = 48) | Luminal A (n = 27) | Luminal B (n = 8) | HER2 (n = 4) | Basal-like (n = 8) | Normal-like (n = 1) |
|---|---|---|---|---|---|---|
| Not available | 2 | 2 | 0 | 0 | 0 | 0 |
| Tumor volume $(mm^3)$* | 6586 (29-40894) | 6775 (29-40894) | 7505 (34-17475) | 3827 (490-11545) | 7222 (161-24447) | 56 (56-56) |
| *Invasive cancer* | | | | | | |
| Ductal | 40 | 23 | 5 | 4 | 7 | 1 |
| Lobular | 8 | 4 | 3 | 0 | 1 | 0 |
| *ER Status* | | | | | | |
| Positive | 40 | 26 | 8 | 3 | 2 | 1 |
| Negative | 8 | 1 | 0 | 1 | 6 | 0 |
| *PR Status* | | | | | | |
| Positive | 35 | 25 | 6 | 1 | 2 | 1 |
| Negative | 13 | 2 | 2 | 3 | 6 | 0 |
| *HER2 status* | | | | | | |
| Positive | 6 | 2 | 0 | 4 | 0 | 0 |
| Equivocal | 15 | 8 | 5 | 0 | 2 | 0 |
| Negative | 25 | 16 | 3 | 0 | 5 | 1 |
| Not Available | 2 | 1 | 0 | 0 | 1 | 0 |
| *Stage* | | | | | | |
| I | 8 | 5 | 1 | 1 | 1 | 0 |
| II | 34 | 20 | 5 | 2 | 7 | 0 |
| III | 6 | 2 | 2 | 1 | 0 | 1 |

Note: --
Unless otherwise indicated, data are number of patients.
*Data for continuous variables are means with ranges in parentheses.

TABLE 2

Association between Luminal B Subtype and Imaging Features

| Feature | PValue |
|---|---|
| *Static Feature* | |
| Volume | .5126 |
| Circularity | .1698 |
| Margin sharpness | .8360 |
| Variance in margin sharpness | .5026 |
| Contrast | .5106 |
| Correlation | .5853 |
| Energy | .0683 |
| Homogeneity | .1244 |
| Entropy | .0523 |
| Variance | .2925 |
| Sum average | .1385 |
| Sum variance | .1517 |
| Sum entropy | .0656 |
| Difference in variance | .5106 |
| Difference in entropy | .1214 |
| Information measure of correlation 1 | .4618 |
| Information measure of correlation 2 | .9363 |
| Maximal correlation coefficient | .5067 |
| *Dynamic feature* | |
| Maximal uptake | 0.0118 |
| F1 (parameters 1) | 0.0015* |
| F2 (parameters 1) | 0.0031 |
| F1 (parameters 2) | 0.5781 |
| F2 (parameters 2) | 0.0492 |

*$P < .0022$ considered to indicate a significant association.

Example 2

Luminal A and Luminal B Molecular Subtypes are Associated with Imaging Features Extracted Following Routine Breast MRI I. Study Methods Patient Population Institutional Review Board approval was secured for the collection and analysis of this Health Information Portability and Accountability Act compliant study with a waiver of informed consent. We retrospectively collected data from a total of 400 consecutive preoperative breast MRIs that were performed between September 2007 and June 2009. We excluded patients undergoing breast cancer treatment at the time of the MRI (e.g., chemotherapy or radiation therapy, N 29), and those with a history of elective breast surgery (e.g., implants or mammoplasty, N 19) or remote prior breast cancer (i.e., those having undergone previous definitive therapy, N 19). Patients without complete pathology data available for review (e.g., hormone receptor status) were excluded (N 42). There were subsequently 291 routine preoperative breast MRIs available for initial review. Cases were then excluded if sequences were missing (N 3) or if there was discordance in the number of slices on the pre and postcontrast sequences (N 1). Finally, in 11 cases, the expert could not confidently describe the features of the biopsy proven cancer and in 1 case the reader did not mark the biopsied lesion, which resulted in a final total of 275 cases available for analysis.

Imaging Data

All preoperative breast MRI scans were performed on either 1.5 Tesla (T) (Signa HDx, GE Healthcare, Little Chalfont, United Kingdom, N 44; Signa HDxt, GE Healthcare, Little Chalfont, United Kingdom, N 5; MAGNETOM Avanto, Siemens, Munich, Germany, N 36) or 3.0 Tesla (Signa HDx, GE Healthcare, Little Chalfont, United Kingdom, N 165; MAGNETOM Trio, Siemens, Munich, Germany, N 25) scanners using a dedicated 7-channel breast coil (Invivo, Orlando, Fla.) with patients in the prone position. On each study there was a precontrast non-fat saturated T1-weighted, a fat saturated T2-weighted, and a fat saturated gradient echo T1-weighted sequence. In addition, using a weight based dosing protocol (0.1 mmol/L per kg body weight) there were three or four dynamic post-contrast T1-weighted gradient echo series with fat suppression obtained following intravenous administration of gadopentetate dimeglumine (Magnevist, Bayer Health Care, Berlin, Germany) or gadobenate dimeglumine (MultiHance, Bracco, Milan, Italy). The specifics of the imaging protocols are shown in Table 3.

Pathology Data

The pathology report from the initial breast biopsy was used to record the estrogen receptor (ER), progesterone receptor (PR), and human epidermal growth factor receptor-2 (HER2) status of each invasive cancer. An Allred score from the immunohistochemical (IHC) stain of greater than or equal to three was considered positive for the ER and PR status. An IHC stain of 3+, or 2+ with confirmation of HER2 gene amplification by FISH (PathVysion Her2 DNA Probe kit, Abbott Laboratories, Chicago, Ill.) was considered positive for the HER2 status. Molecular subtype classification was determined based on the receptor status using established criteria for ER and/or PR positive, HER2 negative, luminal A; ER and/or PR positive, HER2 positive, luminal B; ER and PR negative, HER2 positive, HER2; ER, PR, and HER2 negative, basal; see, Huber et al., *Semin. Radiat. Oncol.* 19 204-210 (2009) and Hayashi et al., *Oncol. Lett.* 5 83-89 (2013), each of which is incorporated by reference herein for their teachings thereof.

Image Annotation

One of six fellowship trained breast imagers with 6, 6, 7, 13, 15, and 20 years of experience annotated each study. Each reader was responsible for annotating a subset of the total cases. The readers used a graphical user interface to draw a box around any areas of mass and non-mass enhancement (up to five lesions). The surgical or image guided biopsy report was then reviewed to identify the lesion for which the pathology results were available. In some cases, the reader may have also identified a satellite lesion for which pathology results were not available, thus this step was taken to ensure that the subsequent computer analysis was performed of the appropriate biopsy proven lesion.

Imaging Feature Extraction

Figure 2:
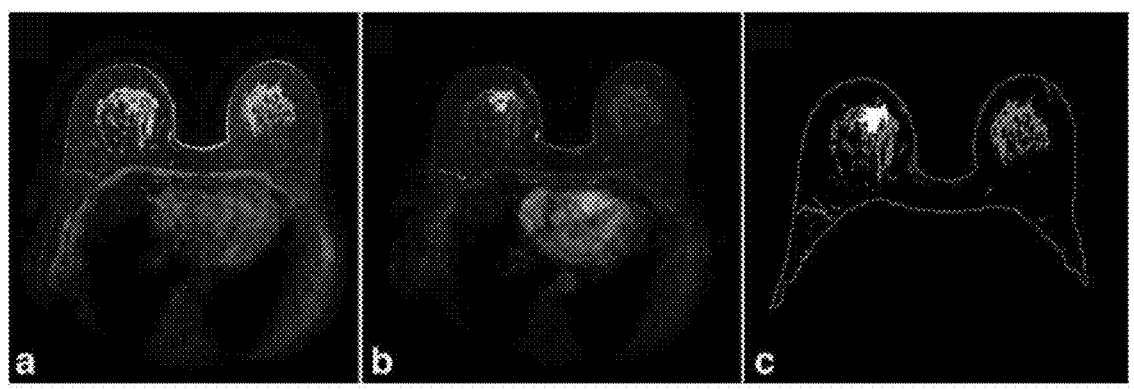
FIG. 2: Representative axial precontrast (a) and postcontrast (b) MR images are shown. The segmentation process (c) differentiates the normal background parenchyma in gray from the lesion in white with the whole breast outlined.

For each case, the enhancement dynamics were extracted automatically using computer vision algorithms after the lesion was marked by the reader. We refer to this process as semiautomatic, because the reader must mark the lesion before the computer vision algorithms can automatically make the appropriate calculations. The N3 method was applied to correct for nonuniformity of intensity. Then, an automatic segmentation algorithm divided the image into the (i) breast, (ii) normal background parenchyma, and (iii) lesion. The segmentation of the breast was performed using a global thresholding method, while the segmentation of the normal background parenchyma and the lesion was performed using the Fuzzy C-Means clustering algorithm. A representative image of the segmentation algorithm is shown in FIG. 2.

Analysis of the MRIs was then performed using 56 different features which can be categorized into four different groups: size and shape, gradient, texture, and dynamic features.

Size and shape features (N=6) refer to major axis length, minor axis length, mean radius length, standard deviation radius length, and volume of the tumor as well as the volume of the background parenchyma. The gradient features (N=2) include the mean and standard deviation of the intensity gradients of the tumor boundary voxels. The texture features (N=14) refer to the Haralick features computed from the subtraction sequences which describe contrast, correlation, energy, homogeneity, entropy, variance, sum average, sum variance, sum entropy, difference variance, difference entropy, two measures of correlation and a max correlation coefficient. The dynamic features (N=34) refer to 16 features that explore the relationship between the enhancement of the tumor and fibroglandular tissue, as described in Mazurowski et al., *Radiology* 273(2) 365-372 (2014) and the 18 features that explore the enhancement dynamics of the lesion and fibroglandular tissue, as described in Chen et al., *Med. Phys.* 31 1076-1082 (2004), each of which is incorporated by reference herein for their teachings thereof.

This study included data collected from patients from four different institutions, which might have included different imaging protocols including different contrast material injection protocols and different time resolution of post-contrast sequences. Despite the variations in image acquisition technique and potentially different equipment among institutions, the statistically significant nature of our results suggests that these findings are robust. As a result of including data from different institutions, we believe that the importance of these results is not unique to specific imaging equipment and protocols.

These results showed that automatically extracted features from breast MR imaging examinations can be used to help identify the breast cancer molecular subtype. Furthermore, this study demonstrates that imaging features are related to breast cancer subtypes, thus providing clinical methods for identifying breast cancer molecular subtype without formal genetic analysis, which can provide a clinical benefit.

Statistical Analysis

For each molecular subtype, we constructed a binary multivariate logistic regression model (function glm with family="biNomial" in R) to determine whether the imaging features are collectively associated with each subtype. Each subtype was binarized (e.g., 1 if it was a particular subtype and 0 if it was any other subtype) and analysis was then performed for each individual subtype. A feature reduction step was performed to remove features that were highly correlated with other features (Irl>0.9, fiNdCorrelatioN function in R). To assess whether each individual subtype was associated with the imaging features, a likelihood ratio test (lrtest function in R) was performed with a P-value of 0.0125 (0.05/4) considered significant. Additionally, as an exploratory analysis, we investigated which features were the most predictive of subtypes by evaluating univariate models that related each individual feature to the binarized subtypes.

II. Study Results

There were 275 women included for analysis. The patient demographics broken down by molecular subtype are shown in Table 4. The average age was 53 years (range: 22-80 years). The majority of the women were white, non-Hispanic (70.2%, 193/275) and postmenopausal (58.2%, 160/275).

The distribution of invasive breast cancers by molecular subtype was as follows: 184 luminal A, 28 luminal B, 17 HER2, and 46 basal.

The multivariate models showed that the imaging features were able to predict luminal A (P=0.0007) and luminal B (P=0.0063) molecular subtype, but not HER2 (P=0.2465) or basal (P=0.1014) molecular subtype. The exploratory analysis of individual features showed that there were two imaging features that were each able to predict both luminal A and luminal B subtype at the P<0.1 level: F1 (0.05, 0.1) and peak location. F1 is a dynamic feature that refers to the ratio of enhancement of the tumor to the fibroglandular tissue at two time points. A descriptive example of F1 is shown in FIG. 2. Peak location is a dynamic feature that refers to the sequence number at which peak enhancement occurs. For example, in a case with 1 pre- and 4 post-contrast sequences, if the peak enhancement occurs in the 3rd post-contrast sequence, then the peak location is 4. The results of the univariate analysis demonstrated P values of 0.0138 and 0.0937 for F1 (0.05, 0.1) for luminal A and luminal B respectively. For peak location, the P values were 0.0170 and 0.0427 for luminal A and luminal B, respectively. There were other features that showed an association with individual subtypes but no other ones that were predictive of both luminal A and luminal B (Table 5).

The total number of cases included in our study is relatively large, but due to the natural distribution of molecular subtypes, there were relatively few cases of luminal B and HER2 subtypes. Thus, it is possible that the lack of a statistically significant association between imaging features and HER2 or basal subtypes was only due to a limited sample size and not due to the lack of an association.

One of the strengths of this study was that we used six expert radiologists in the interpretation of our studies with each case annotated by one radiologist. This approach ensures that these findings are not unique to the annotation abilities of any one radiologist.

We demonstrated that semi-automatically extracted features from breast MRIs can be used to identify breast cancer molecular subtype. To our knowledge, this is the largest study to date and the only study which has been able to show an association between imaging features and multiple different breast cancer molecular subtypes. Using imaging data to identify molecular subtypes may allow radiologists to provide valuable additional clinical information to referring providers with minimal additional cost, time, or infrastructure investment.

TABLE 3

Breast MRI Protocols by Scanner for the Dynamic Sequences

| Scanner | Field strength (T) | TR | TE | FOV (cm) | Matrix size |
|---|---|---|---|---|---|
| Signa HDx/HDxt | 1.5 | 5.3 | 2.4 | 38 | 350 × 350 |
| MAGNETOM Avanto | 1.5 | 4.0 | 1.3 | 36 | 448 × 448 |
| Signa HDx | 3.0 | 5.7 | 2.4 | 34 | 350 × 350 |
| MAGNETOM Trio | 3.0 | 4.1 | 1.4 | 36 | 448 × 448 |

TABLE 4

Patient Demographics Overall and by Molecular Subtype

| Characteristic | Patients (N = 275) | Luminal A (N = 184) | Luminal B (N = 28) | HER2 (N = 17) | Basal (N = 46) |
|---|---|---|---|---|---|
| Age, years (range) | 53 (22-80) | 54 (28-80) | 49 (30-68) | 50 (34-65) | 54 (22-73) |
| Race/Ethnicity | | | | | |
| White non-Hispanic | 193 | 132 | 23 | 11 | 27 |
| Black | 64 | 38 | 4 | 5 | 17 |
| Asian | 5 | 3 | 1 | 0 | 1 |
| Native American | 3 | 3 | 0 | 0 | 0 |
| Hispanic | 2 | 2 | 0 | 0 | 0 |
| Multiracial | 1 | 1 | 0 | 0 | 0 |
| Native Hawaiian or Pacific Islander | 1 | 0 | 0 | 0 | 1 |
| Not reported | 6 | 5 | 0 | 1 | 0 |
| Menopausal status | | | | | |
| Pre-menopausal | 113 | 74 | 13 | 7 | 19 |
| Post-menopausal | 160 | 108 | 15 | 10 | 27 |
| Not reported | 2 | 2 | 0 | 0 | 0 |

TABLE 5

Features with a P Value Less than 0.1 From Univariate Modeling

| Subtype | Feature | P value |
|---|---|---|
| Luminal A | F1 (0.05, 0.1)P2 | 0.0138 |
| | Peak location | 0.0170 |
| | Major axis length | 0.0255 |
| | Diff variance | 0.0314 |
| | Sum variance | 0.0401 |
| | Volume | 0.0560 |
| | F2(0.5, 0.1)P2 | 0.0610 |
| | Max uptake | 0.0808 |
| Luminal B | Peak location | 0.0427 |
| | Gradient mean | 0.0541 |
| | F1(0.05, 0.1)P2 | 0.0541 |
| | F1(0.05, 0.8) | 0.0860 |
| HER2 | Peak location of enhancement variance | 0.0014 |
| | Major axis length | 0.0398 |
| | Diff variance | 0.0499 |
| Basal | Sum variance | 0.0419 |
| | Max uptake | 0.0812 |
| | Volume | 0.0879 |

Example 3

Breast Cancer Progression-Free Survival is Associated with MRI Tumor Enhancement Dynamics I. Study Methods Patient Population Institutional Review Board (IRB) approval was secured for this study. We retrospectively collected data from 400 consecutive preoperative contrast enhanced breast MRIs from September 2007 through June 2009. Patients with a history of elective breast surgery (e.g., implants or mammoplasty, n=19) or remote prior breast cancer (i.e., those having undergone previous definitive therapy, n=19), as well as those undergoing breast cancer treatment at the time of the MRI (e.g., chemotherapy or radiation therapy, n=29) were excluded. Additionally, patients with missing pathology data (e.g., tumor grade) were excluded (n=42). This resulted in 291 patients with preoperative breast MRIs available for analysis. After a review of the imaging sequences, cases were excluded if they were missing sequences (n=3) or if the number of slices were different between pre and postcontrast sequences (n=1). Finally, 11 cases were skipped by the expert readers during the annotation process because the features of the main abnormality could not be assessed (e.g., abnormality was obscured). Finally, in 1 case the reader did not mark the biopsied lesion. The final total of cases included for analysis was 275.

Imaging Data

All breast MRI scans were acquired using a 1.5 Tesla (Signa HDx, GE Healthcare, Little Chalfont, United Kingdom, n=44; Signa HDxt, GE Healthcare, Little Chalfont, United Kingdom, n=5; MAGNETOM Avanto, Siemens, Munich, Germany, n=36) or 3.0 Tesla (Signa HDx, GE Healthcare, Little Chalfont, United Kingdom, n=165; MAGNETOM Trio, Siemens, Munich, Germany, n=25) scanner in the prone position with a dedicated 7-channel breast coil (Invivo, Orlando, USA). Each study included a precontrast non-fat saturated T1-weighted and a fat saturated gradient echo T1-weighted sequence. All but one study included a fat saturated T2-weighted sequence. Then, typically four (except for 3 cases which had two or three) dynamic postcontrast T1-weighted gradient echo series with fat suppression were obtained following intravenous administration of gadopentetate dimeglumine (Magnevist, Bayer Health Care, Berlin, Germany) or gadobenate dimeglumine (MultiHance, Bracco, Milan, Italy), via a weight based dosing protocol. All images were acquired in the axial plane.

Clinical Data

The following information was obtained from the medical records: patient age, race/ethnicity, menopausal status, tumor grade, time to progression, and time to last follow up. Clinical data were available for review through April 2013, per the specifications of our IRB protocol. Race and ethnicity were self-reported in the medical record: white non-Hispanic, black, Asian, Native American, Hispanic, multiracial, native Hawaiian or Pacific Islander, or not reported. Menopausal status was collected from the clinic notes at the time of diagnosis: pre-menopausal, post-menopausal, or not reported. Tumor grade (Low, Intermediate, or High) was recorded from the pathology report of the initial specimen biopsy. The time to progression was defined as the difference between the date of initial biopsy and the date that a recurrence was first detected or date of death if no recurrence event was noted. The time to last follow up was defined as the difference between the date of initial biopsy and the last clinic visit that occurred within the study follow up period.

Image Annotation

Six fellowship-trained breast imagers with 6-20 years of post-fellowship experience annotated the imaging data. Each reader was assigned a subset of cases for annotation such that each case was annotated by one reader. The readers identified each mass and non-mass enhancement (up to 5 per study) by drawing a box around it. The annotated mass or non-mass enhancement that corresponded to the location description from the surgical or image guided biopsy report in the medical record was then quantified by the computer algorithm. In our approach, the radiologist does not have to identify the exact boundaries of the abnormality or normal breast parenchyma. This was done by computer algorithms as described in the next section.

Computer-Based Image Segmentation and Feature Extraction

For each case, based on the bounding box for a biopsied abnormality drawn by an expert, we assessed the enhancement dynamics feature automatically using computer vision algorithms implemented in our laboratory in the following way.

First, the chest region was removed automatically by a polynomial curve fitting algorithm and the breast region was detected automatically by a global thresholding and an active contour method. Second, the mass region and the background parenchyma within the breast were segmented automatically using the Fuzzy C-Means (FCM) clustering algorithm. By automatically identifying the background breast parenchyma and the tumor regions, the computer algorithm removes the onus of identifying those regions from the radiologist and introduces a reproducible and reliable method for describing the enhancement of the background breast parenchyma and the tumor.

Following the segmentation process, the levels of enhancement in the tumor region as well as the background parenchyma were assessed by the algorithm. When the proportion of enhancing background parenchyma reached a predetermined threshold, the ratio of average tumor enhancement to maximal tumor enhancement (a dynamic feature F) was then recorded.

The ratio of tumor enhancement at a time point determined by the rate of background parenchymal enhancement, allows the internally normalization of the tumor enhancement quantification. By being internally normalized, the quantified ratio of tumor enhancement is immune to differences in the absorption rate of contrast material, sequence timing between imaging protocols, magnet field strengths, and scanner manufacturers.

Figure 3:
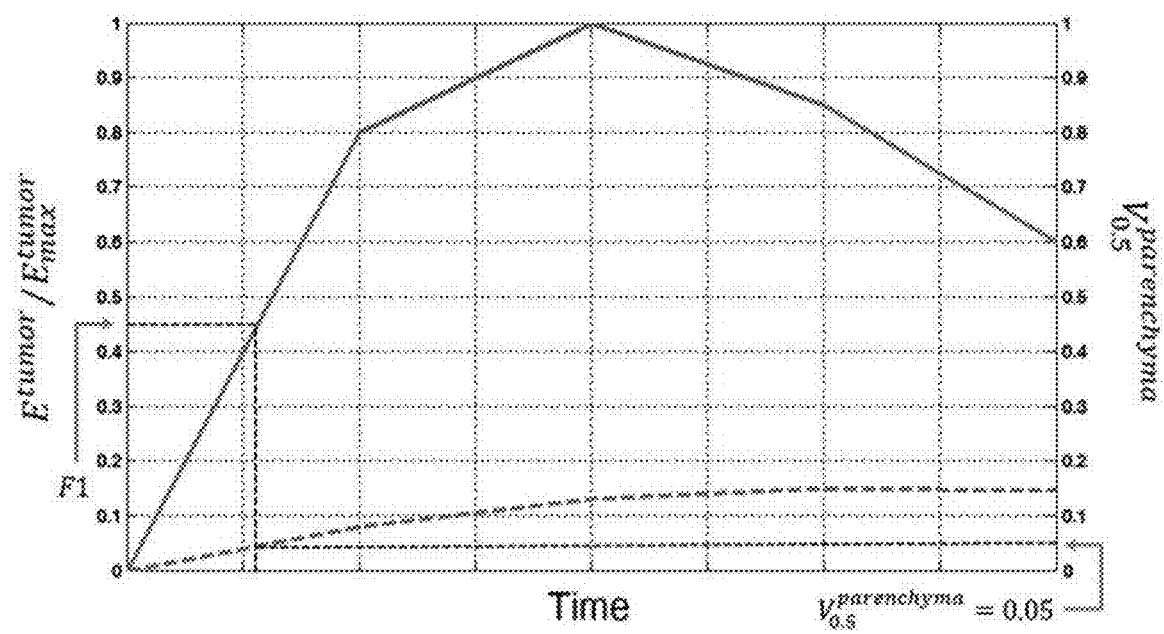
FIG. 3. Graph illustrating the extraction of dynamic feature F1 with parameters T11=0.05 and T12=0.5 is shown. First, the time when the volume of the enhancing background parenchyma (dashed line) is 0.05 of the total background parenchyma volume is determined. The corresponding enhancement value of the tumor (solid line) at this time is equal to F1.
Figure 4:
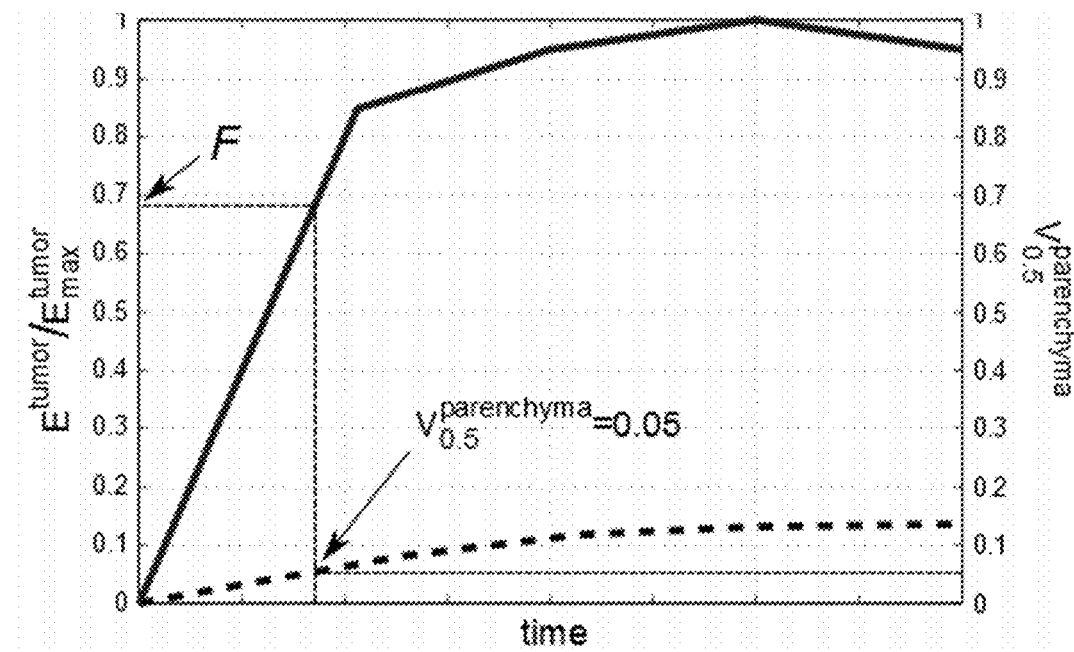
FIG. 4. Graph illustrating extraction of the dynamic feature F1 with parameters $T_{11}$=0.05 and $T_{12}$=0.5. First, the time is determined when the volume of the enhancing background parenchyma reaches 0.05 of the total volume background parenchyma. Then, the algorithm calculates the feature F1 as the enhancement of the tumor at that time.
Figure 5A:
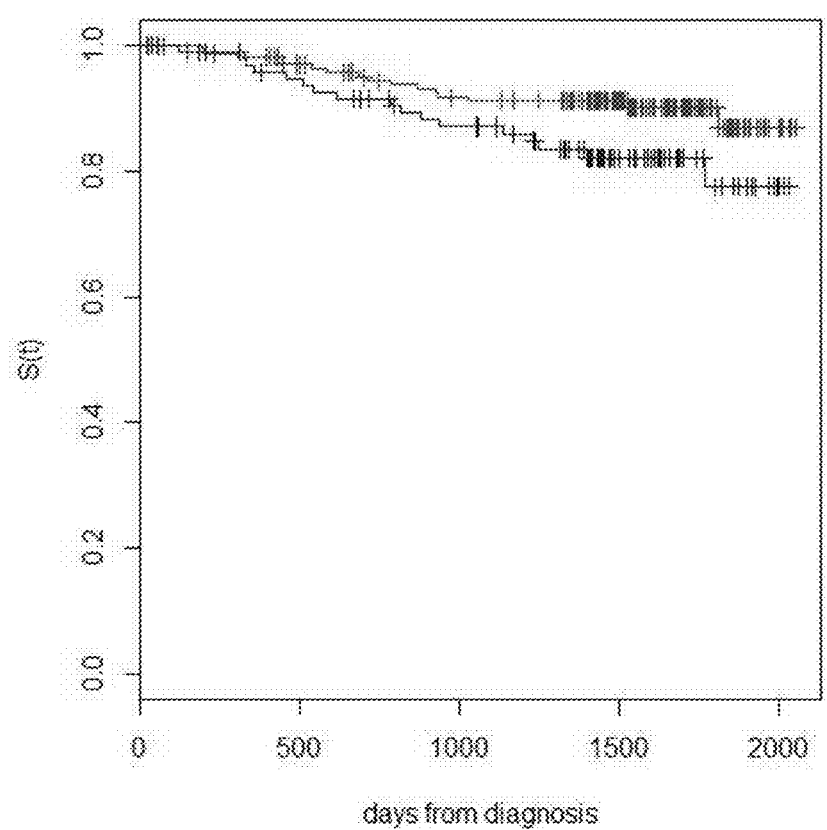
FIGS. 5A-5B. Plot illustrating how the proposed feature F1 distinguishes patients with poor and good recurrence-free survival. (A) shows survival curves for patients with F1 value less than 0.5 (red curve) and those with F1 value higher or equal to 0.5 (blue curve). (B) shows survival curves for patients with F1 value less than 1 (red curve) and those with F1 value equal to 1 (blue curve).
Figure 5B:
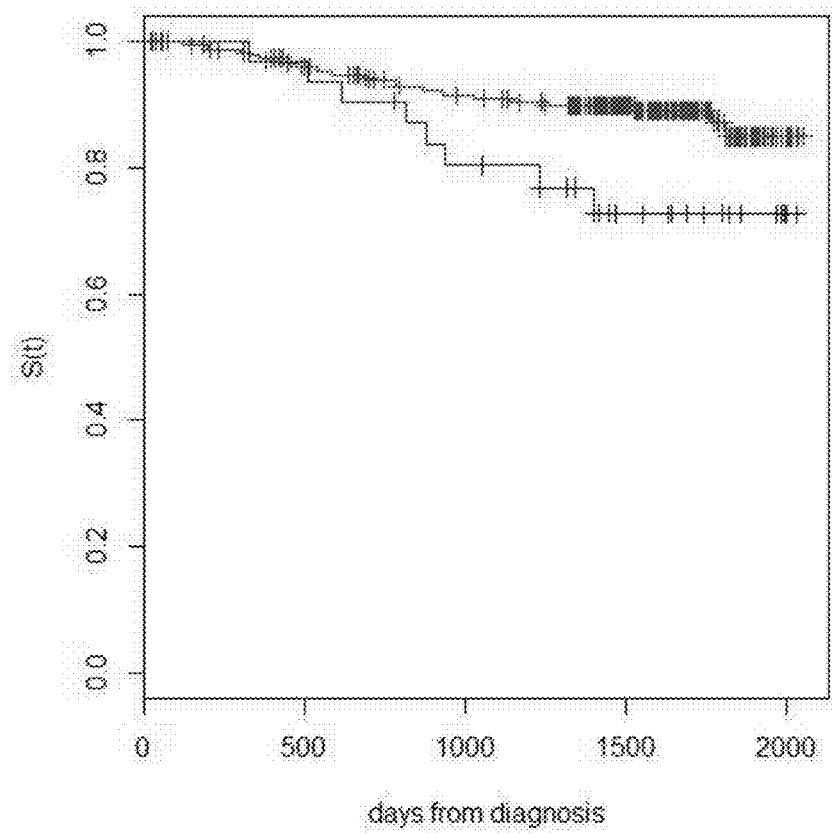

Based on the semi-automatic segmentation of the tumor, the major axis length defined as the longest diameter of the tumor on a single slice was further extracted. FIG. 3 shows an illustration of the feature extraction process based on the enhancement plots.

Statistical Analysis

To assess whether the extracted dynamic feature F was associated with progression-free survival, we constructed a Cox proportional hazards regression model. We used the coxph function in R for this purpose. To control for patient age, menopausal status, race, tumor grade, and tumor size, we also included these variables in the model. A p-value less than 0.05 was considered statistically significant.

Patient age and tumor size were available for all patients and were included in the model with no modifications. We substituted the one missing value for the tumor grade with intermediate grade (the most common grade in our dataset). For simplicity, we also binarized the race/ethnicity variable such that white non-Hispanic (majority in our dataset) was assigned a value of 0 and all other races were assigned a value of 1. Then, the 6 missing values for this variable were assigned a 0 or 1 randomly according to the distribution observed in the remainder of the dataset. The 2 missing values for the menopausal status were also filled in randomly according to the distribution observed in the dataset.

II. Study Results

There were 275 women included in the study dataset. The median age was 53 years (range: 22-80). White, non-Hispanic was the most common race and ethnicity (70.2%, 193/275), followed by black (23.3%, 64/275). Postmenopausal status was observed for 58.2% (160/275) of women and 41.1% (113/275) women were premenopausal, with menopausal status not reported in 2 women. The median tumor length of the major axis was 31 mm (range: 4-157). Tumor grade was distributed as follows: low—51 patients, intermediate—142 patients, high—81 patients. Tumor grade was not available for 1 patient. There were 33 progression events, with a median progression-free follow up of 1494 days (range: 22-2051). The full patient and tumor characteristics along with mean follow up time and number of progression events are presented in Table 6.

The multivariate survival analysis showed that the semi-automated tumor enhancement quantification (i.e. the dynamic feature F) is independently predictive of progression-free survival (p=0.024), after controlling for patient age, race/ethnicity, menopausal status, tumor grade, and tumor size. This dynamic feature represents the rate of enhancement of the tumor versus the background breast parenchymal enhancement, and the survival regression model indicated that a higher feature value was associated with an increased risk of disease progression.

This study has demonstrated that patient progression-free survival in breast cancer is independently associated with a semi-automatically extracted breast MRI feature which quantifies the enhancement dynamics of the tumor compared with the background parenchymal enhancement. Specifically, an increase in the relative tumor enhancement rate corresponds to an increase in the risk of cancer recurrence.

An advantage of this approach is that computer algorithms can be applied to quantitatively assess the enhancement dynamics of the tumor and background breast parenchyma and extract a single summarizing feature. The comprehensive (all voxels in tumor and parenchyma) and quantitative nature of the feature extraction process precludes assessment by human readers. Furthermore, as compared to some dynamic features that can be assessed by human readers, the semi-automatic nature of our approach results in dramatically reduced inter- and intra-observer variability because the actual measurement is conducted by the computer algorithm. The automatic nature of the extraction also means that the benefits of quantitative measurement are provided with minimal additional burden to the radiologist. Therefore, these methods do not significantly increase the interpretation time or cost to the patient.

Thus, these results demonstrate that a semi-automatically extracted feature quantifying tumor and background parenchymal enhancement dynamics on pre-operative breast MRI is independently associated with progression-free survival among patients newly diagnosed with breast cancer. The potential to incorporate prognostic value to routine breast MRI could increase the utility of pre-operative MRI and provide referring providers with valuable additional information.

TABLE 6

Patient Demographics and Tumor Characteristics

| Characteristic | Patients (n = 275) |
|---|---|
| Age (years) | 53 |
| Race/Ethnicity | |
| White non-Hispanic | 193 |
| Black | 64 |
| Asian | 5 |
| Native American | 3 |
| Hispanic | 2 |
| Multiracial | 1 |
| Native Hawaiian or Pacific Islander | 1 |
| Not reported | 6 |

TABLE 6-continued

Patient Demographics and Tumor Characteristics

| Characteristic | Patients (n = 275) |
|---|---|
| Menopausal status | |
| Premenopausal | 113 |
| Postmenopausal | 160 |
| Not reported | 2 |
| Tumor grade | |
| Low | 51 |
| Intermediate | 142 |
| High | 81 |
| Not available | 1 |
| Tumor major axis length (mm) | 31 |
| Follow up (days) | 1494 |
| Progression events | 33 |

Example 4

Algorithmically-Assessed MRI Enhancement Dynamics Identify a Highly Favorable Subset of Patients Among Those with Large, Hormone Receptor Positive Breast Cancers I. Study Methods
Patient Population An Institutional Review Board approval was secured for this study. We retrospectively collected data on 400 consecutive patients who underwent preoperative dynamic contrast enhancement MRIs in the period from September 2007 through June 2009 at our institution. Our study excluded patients that had remote prior breast cancer (n=19), those undergoing breast cancer treatment at the time of the MRI (n=29), those that had missing pathology data (n=42), and majority of the patients that had a history of elective breast surgery (n=19). We further excluded patients with metastatic cancer at presentation (n=6) and those who had a date of death but no date of recurrence recorded (n=2). Following the review of the MRIs, we also excluded cases that had missing sequences (n=3), cases with different number of slices for pre and post-contrast sequences (n=1) and those that were skipped by the expert readers (n=11) since the abnormality features could not be assessed (e.g. obscured abnormality) or the biopsied lesion was not marked by the expert reader (n=1). This resulted in a set of 267 cases that were used in our study.

Imaging Data and Image Annotation

Axial DCE-MRI scans were acquired using 1.5 Tesla (n=82) and 3.0 Tesla (n=185) scanners in the prone position. All the included studies contained a pre-contrast non-fat saturated T1-weighted sequence and a fat-saturated gradient echo T1-weighted sequence. Usually 4 post-contrast T1-weighted sequences with fat suppression were acquired after administration of contrast agent (gadopentetate or gadobenate dimeglumine). Three cases had only 2 or 3 post-contrast sequences.

The images were annotated by six fellowship-trained breast imaging radiologists with 6-20 years of post-fellowship experience. Each case was annotated only by 1 of the readers. For each case, the reader identified up to 5 lesions (mass/non mass enhancement) by drawing a rectangular cuboid (i.e. a rectangular box) around the lesion using an in-house graphical user interface.

Algorithmic Image Analysis

We conducted semi-automatic analysis of the images using algorithms implemented in our laboratory. Specifically, using the boxes drawn by expert radiologist that outline the tumor as well as the outline of the breast, we used Fuzzy C-Means clustering algorithm to find the exact outline of the tumor and segment normal breast parenchyma from fatty tissue.

Following segmentation of the breast into different regions, we applied an analysis of the enhancement patterns. Our analysis allows for comparing enhancement of the tumor with enhancement of normal breast parenchyma. Specifically, for each case we found enhancement of the tumor (proportion of maximum enhancement) at the time when the proportion of volume of the enhancing normal breast parenchyma reaches the predefined level $T_2$. The formal definition of the feature (F) follows:

$$F = \frac{E^{TUM,avg}(\min\{t: V^{BP}_{T_1}(t) = T_2\})}{\max_t(E^{TUM,avg}(t))}$$

where $$V^{BP}_{T_1}(t) = \frac{|(x, y, z) \in BP: E(x, y, z, t) > T_1 \cdot \max_t(E^{TUM,avg}(t))|}{|BP|}$$

$$E^{TUM,avg}(t) = \frac{\Sigma_{x,y,z \in TUM} E(x, y, z, t)}{|TUM|}$$

$$E(x, y, z, t) = \frac{I(x, y, z, t) - I(x, y, z, 0)}{I(x, y, z, 0)}$$

In the above formulas, I(x,y,z,t) is an intensity of a voxel located at the (x,y,z) coordinates at the time t. TUM is the set of tumor voxels and BP is the set of background parenchyma voxels. $T_1$ and $T_2$ are constant parameters. The parameters were set to $T_1$=0.5 and $T_2$=0.05.

Statistical Analysis

In order to analyze prognostic value of the biomarker for patients with different characteristics, we divided the patient population using two criteria. The first criterion was the receptor status/molecular subtype. Specifically, we divided patients into those that had estrogen and/or progesterone positive and HER2 negative tumors and all other patients. The ER and/or PR+, HER2− group is the most common one and these characteristics are associated with Luminal molecular subtypes. Since full molecular subtyping requires gene expression or proliferation index data, we will call these tumors Luminal-like, consistent with various breast cancer management guidelines. Splitting patients this way allows us to obtain the most balanced division using receptor status, and defines the subgroup where the imaging biomarker is most clinically useful. The second criterion was the tumor size. We used the median size in terms of major axis length to split the patients into two groups. This resulted in four groups: (1) Luminal-like, large tumors, (2) Luminal-like, small tumors, (3) non-Luminal-like, large tumors, and (4) non-Luminal-like small tumors.

Within each of these groups, we evaluated the prognostic value of our imaging feature by dividing the patients in the group into those that had a high value of the feature and those that had a low value. The threshold was selected to be 0.8 based on observed natural grouping of those values into two separate clusters (i.e. a bimodal distribution), particularly for Luminal-like patients. Following the division, we calculated the hazard ratio between the patients with low and high value of the feature and plotted Kaplan-Meier curves. Distant recurrence was used as the event of interest in the survival analysis.

To further evaluate whether the proposed imaging feature has a prognostic value in addition to other features, for each of the receptor status and size-based groups, we created a multivariate Cox proportional hazards regression model in which we controlled for potentially confounding variables by including them in the model. Specifically, the covariates in the model were: the proposed dynamic imaging feature, tumor size, tumor grade, node involvement, patient race/ethnicity, patient age, and patient menopausal status. For simplicity, the patient race/ethnicity variable was binarized into two values: 0 for white non-Hispanic (majority in our dataset), and 1 for all other races.

Since occasional values for some of the variables were missing in our data, for the purpose of this analysis, we filled them in the following way. For the missing value of the patient race/ethnicity, menopausal status, and node involvement, we used a randomly generated value according to the distribution observed in our data. For tumor grade, since only 1 value was missing, we used the most common value as the replacement.

II. Study Results

We analyzed data for 267 women. Important patient and data characteristics are listed in Table 7. The median tumor size according to our algorithmic measurement was 31.3 mm and this value was used as the threshold to distinguish small and large tumors. We found that for ER and/or PR+, HER2− large tumors (major axis ≥31.3 mm), our imaging-based biomarker provides a very strong prognostic value of distant recurrence-free survival demonstrated by the Kaplan-Meier curves in FIG. 2(A) and the corresponding hazard ratio of 9.29 (95% CI:2.22-3895). We confirmed that the proposed imaging feature is prognostic of outcomes even after further controlling for size, tumor grade, node involvement, patient race/ethnicity, patient age, and patient menopausal status (p=0.011). For non-Luminal-like patients with large tumors (major axis ≥31.3 mm) we observed a hazard ratio of HR=1.65 (95% CI:0.20-13.86) which was not statistically significantly different from 1 (i.e., no significant difference in hazard between the two groups).

The results for patients with smaller tumors (major axis <31.3 mm) are shown in FIGS. 2C and 2D. While a difference in the survival curves for patients with low and high value of the feature was observed, the hazard ratios are ill-defined due to the absence of distant recurrence events in one group. Therefore we cannot draw any conclusions for these cases.

TABLE 7

Patient and tumor characteristics. Median and IQR are reported for patient age, tumor major axis length and follow up time.

| Characteristic | Patients (n = 267) |
|---|---|
| Age (years) | 53 (46-61) |
| Race/Ethnicity | |
| White non-Hispanic | 186 |
| Black | 63 |
| Asian | 5 |
| Native American | 3 |
| Hispanic | 2 |
| Multiracial | 1 |
| Native Hawaiian or Pacific Islander | 1 |
| Not reported | 6 |

TABLE 7-continued

Patient and tumor characteristics. Median and IQR are reported for patient age, tumor major axis length and follow up time.

| Characteristic | Patients (n = 267) |
|---|---|
| Menopausal status | |
| Premenopausal | 110 |
| Postmenopaaisal | 155 |
| Not reported | 2 |
| Receptor status | |
| Luminal-like: | 183 |
| ER+, PR+, HER2− | 156 |
| ER+, PR−, HER2− | 19 |
| ER−, PR+, HER2− | 8 |
| Non-luminal: | 84 |
| ER+ and/or PR+, HER2+ | 26 |
| ER−, PR−, HER2+ | 14 |
| ER−, PR−, HER2− | 44 |
| Tumor grade | |
| Low | 51 |
| Intermediate | 139 |
| High | 76 |
| Not available | 1 |
| Node involvement | |
| N0 | 157 |
| N1 | 72 |
| N2 | 21 |
| N3 | 13 |
| Not available | 4 |
| Tumor major axis length (mm) | 31 (20-50) |
| Follow up (year) | 4.1 (3.6-5.6) |
| Distant recurrence events | 22 |

In this study we demonstrated that MRI enhancement dynamics as captured by computer algorithms implemented in our laboratory can distinguish patients with high and low risk of distant recurrence among breast cancer patients with large ER and/or PR+, HER2− tumors.

By conducting this evaluation, we place our analysis in a relevant clinical context where ER and/or PR+, HER2− tumors are treated very differently than HER2+ and triple negative tumors. Large ER and/or PR+, HER2− tumors, for which our biomarker showed very strong prognostic value, are of strong interest since some of these could be spared chemotherapy without increasing their risk of distant recurrence and thus potentially avoid unnecessary treatment, side effects and associated costs. In this study, we showed that our biomarker has very strong prognostic power for this group of patients.

Another important finding from our work is that in terms of prognostic value, MRI enhancement dynamics as quantified by our feature do not simply duplicate tumor molecular subtype (receptor status-based surrogate) but provide additional strong prognostic value within the Luminal-like subtype. The current work demonstrates that prognostic signatures can be identified within cancers of a particular molecular subtype.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of the specified embodiments. All of the various embodiments, aspects, and options disclosed herein can be combined in all variations. The scope of the compositions, formulations, methods, and processes described herein include all actual or potential combinations of embodiments, aspects, options, examples, and preferences herein described. In particular, the methods and systems described herein have been exemplified for assessing breast cancer subtype and prognosis. However, it is contemplated that the methods and systems described herein may be useful in providing prognostic information for other types of cancer. All patents and publications cited herein are incorporated by reference herein for the specific teachings thereof.

What is claimed is:

1. A method of treating a subject having a breast cancer disease comprising one or more breast cancer lesions, the method comprising:
   a) evaluating the one or more breast cancer lesions from a magnetic resonance image (MR image) of a breast tissue from the subject, wherein the evaluation comprises:
      (i) marking one or more boundaries of the one or more of the breast cancer lesions in the MR image;
      (ii) correcting non-uniformity of intensity of the MR image;
      (iii) segmenting the MR image into one or more tissue segments, wherein the tissue segments comprise one or more than one of a normal background parenchyma, breast cancer lesion tissue, or other breast tissue;
      (iv) extracting one or more image features from the MR image, wherein the one or more extracted image features comprise one or more dynamic enhancement-based features that assess the enhancement of the breast cancer lesion tissue segment over time, the one or more dynamic enhancement-based features comprising at least one of:
         (A) feature F1, which comprises a ratio of (1) an average level of breast cancer lesion image enhancement at a time point when a predetermined fraction of normal background parenchyma reaches a predetermined threshold level of image enhancement to (2) a maximum average level of breast cancer lesion image enhancement from across all time points, or
         (B) feature F2, which comprises a fraction of normal background parenchyma that is above a predetermined threshold level of image enhancement at a time point when an average level of breast cancer lesion enhancement divided by a maximum average level of breast lesion enhancement from across all time points reaches a predetermined threshold; and
      (v) providing a score based on the one or more extracted image features, wherein the score is indicative of a likelihood of breast cancer disease progression or recurrence, an overall survival of the subject, a recurrence-free survival of the subject, a distant recurrence-free survival of the subject, a response by the subject to neo-adjuvant therapy or a combination thereof; and
   b) treating the subject based on the score, wherein treating the subject comprises initiating a standard of care medical treatment, increasing a medical treatment, decreasing a medical treatment, altering a medical treatment, or ceasing a medical treatment.

2. The method of claim 1, wherein correcting non-uniformity of intensity comprises performing a nonparametric non-uniform intensity normalization method on the marked MR image.

3. The method of claim 1, wherein segmentation of the normal background parenchyma is based on fat-saturated MR images, non-fat saturated MR images, or both.

4. The method of claim 1, wherein the segment of other breast tissue is obtained by performing a global thresholding method on the MR image.

5. The method of claim 1, wherein the normal background parenchyma and the breast cancer lesion tissue segments are obtained by performing Fuzzy C-Means clustering.

6. The method of claim 1, wherein the one or more extracted image features further comprise one or more of:
    (a) texture features;
    (b) size features;
    (c) shape features, either two-dimensional or three-dimensional;
    (d) gradient features;
    (e) features quantifying imaging-based heterogeneity of the one or more breast cancer lesions; and
    (f) features quantifying spatial kinetics of the one or more breast cancer lesions.

7. The method of claim 6, wherein the size features or shape features comprise one or more of a major axis length, a minor axis length, a mean radius length, a standard deviation of the radius length, a volume of the breast cancer lesion, a volume of the normal background parenchyma, circularity, and features based on three-dimensional analysis of the MR images.

8. The method of claim 6, wherein the gradient features comprise a mean and a standard deviation of one or more intensity gradients of one or more breast cancer lesion boundary voxels.

9. The method of claim 6, wherein the texture features comprise at least one or more Haralick texture features.

10. The method of claim 1, wherein the one or more dynamic enhancement-based features comprise the feature F1.

11. The method of claim 1, wherein the one or more dynamic enhancement-based features comprise the feature F2.

12. The method of claim 1, wherein the feature F1 and the feature F2 are calculated according to Formula I or Formula II, respectively:

$$F1 = \frac{E^{tumor}\left(V_{T_{12}}^{parenchyma}(t) = T_{11}\right)}{E_{max}^{tumor}} \quad \text{Formula I}$$

$$F2 = V_{T_{22}}^{parenchyma}\left(\frac{E^{tumor}(t)}{E_{max}^{tumor}} = T_{21}\right); \quad \text{Formula II}$$

wherein for Formulae I and II:

$$E^{tumor}(t) = \frac{I^{tumor}(t) - I_{pre}^{tumor}}{I_{pre}^{tumor}}$$

$$V_{T_{22}}^{parenchyma}(t) = \frac{n(E^{parenchyma}(t) > T_{22} \cdot E_{max}^{tumor})}{n^{parenchyma}}$$

$$E^{parenchyma}(t) = \frac{I^{parenchyma}(t) - I_{pre}^{parenchyma}}{I_{pre}^{parenchyma}};$$

and, wherein $T_{11}$, $T_{12}$, $T_{21}$, and $T_{22}$ may each range from 0-1.

13. The method of claim 12, wherein the one or more dynamic enhancement-based features comprise the feature F1 and wherein $T_{11}$ is 0.05 and $T_{12}$ is 0.5 or $T_{11}$ is 0.05 and $T_{12}$ is 0.1.

14. The method of claim 12, wherein the one or more dynamic enhancement-based features comprise the feature F2 and wherein $T_{21}$ is 0.8 and $T_{22}$ is 0.5 or $T_{21}$ is 0.5 and $T_{22}$ is 0.1.

15. The method of claim 12, wherein the one or more dynamic enhancement-based features comprise the feature F1 and wherein a value of the feature F1 greater than 0.75 is indicative of an increased risk of breast cancer disease recurrence.

16. The method of claim 12, wherein the one or more dynamic enhancement-based features comprise the feature F1 and wherein:
    a) a value of the feature F1 greater than 0.75; and
    b) a peak enhancement location before a second post-contrast sequence,
    together are indicative of luminal A or luminal B breast cancer.

17. The method of claim 12, wherein the one or more dynamic enhancement-based features comprise the feature F1 and wherein:
    $T_{11}$ is 0.05 and $T_{12}$ is 0.1; or
    $T_{11}$ is 0.02 and $T_{12}$ is 0.5; or
    $T_{11}$ is 0.05 and $T_{12}$ is 0.5; or
    $T_{11}$ is 0.1 and $T_{12}$ is 0.5; or
    $T_{11}$ is 0.05 and $T_{12}$ is 0.8; or
    $T_{11}$ is 0.1 and $T_{12}$ is 0.8.

18. The method of claim 1, wherein the medical treatment comprises chemotherapy, hormonal therapy, immunotherapy or combinations thereof.

19. The method of claim 1, wherein the score, alone or in combination with genomic and pathological profile, is used to determine if patients will receive chemotherapy.

20. The method of claim 1, further comprising combining the score with one or more of cancer lesion receptor status, cancer lesion receptor status-based lesion subtype, lesion size, lymph node involvement, commercial genomic assays, PAM50 marker, lesion pathology, other tumor markers, or genomic markers.

21. The method of claim 1, wherein the subject has a breast cancer that is a lymph-node positive or lymph-node negative breast cancer.

22. The method of claim 1, wherein the breast cancer lesion is ER-positive or -negative, PR-positive or -negative, HER2-positive or -negative, or any combination thereof, or wherein the breast cancer lesion is luminal A, luminal B, basal, normal-like or claudin-low.

23. The method of claim 17, wherein the breast cancer lesion is large, ER-positive and/or PR-positive, and HER2-negative.

24. The method of claim 23, wherein a value of the feature F1 greater than or equal to 0.75 is indicative of a lower likelihood of recurrence-free survival.

* * * * *

UNITED STATES PATENT AND TRADEMARK OFFICE
CERTIFICATE OF CORRECTION

PATENT NO. : 10,980,519 B2  
APPLICATION NO. : 15/209212  
DATED : April 20, 2021  
INVENTOR(S) : Mazurowski et al.

Page 1 of 1

It is certified that error appears in the above-identified patent and that said Letters Patent is hereby corrected as shown below:

On the Title Page

Item (12) delete "Mazurowski" and insert --Mazurowski et al.--

Item (72) Inventor, should read:
--(72) Inventors: Maciej Mazurowski, Durham, NC (US); Lars Johannes Grimm, Durham, NC (US); Jing Zhang, Beaumont, TX (US)--

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*